(12) United States Patent
Rothberg et al.

(10) Patent No.: US 10,856,840 B2
(45) Date of Patent: Dec. 8, 2020

(54) UNIVERSAL ULTRASOUND DEVICE AND RELATED APPARATUS AND METHODS

(71) Applicant: Butterfly Network, Inc., Guilford, CT (US)

(72) Inventors: Jonathan M. Rothberg, Guilford, CT (US); Susan A. Alie, Stoneham, MA (US); Nevada J. Sanchez, Guilford, CT (US); Tyler S. Ralston, Clinton, CT (US); Christopher Thomas McNulty, Guilford, CT (US); Jaime Scott Zahorian, Guilford, CT (US); Paul Francis Cristman, New Haven, CT (US); Matthew de Jonge, New York, NY (US); Keith G. Fife, Palo Alto, CA (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 15/415,434

(22) Filed: Jan. 25, 2017

(65) Prior Publication Data

US 2017/0360397 A1   Dec. 21, 2017

Related U.S. Application Data

(60) Provisional application No. 62/352,337, filed on Jun. 20, 2016.

(51) Int. Cl.
*A61B 8/00* (2006.01)
*A61B 8/14* (2006.01)
(Continued)

(52) U.S. Cl.
CPC ............ *A61B 8/145* (2013.01); *A61B 8/12* (2013.01); *A61B 8/54* (2013.01); *B06B 1/0292* (2013.01);
(Continued)

(58) Field of Classification Search
CPC ..... A61B 8/145; A61B 8/4427; A61B 8/4488; A61B 8/4494
See application file for complete search history.

(56) References Cited

U.S. PATENT DOCUMENTS 4,389,601 A   6/1983   Sullivan
4,814,637 A   3/1989   Roessler et al.
(Continued)

FOREIGN PATENT DOCUMENTS

WO   WO 2009/135255 A1   11/2009
WO   WO 2015/028945 A2   3/2015

OTHER PUBLICATIONS

Stmicroeletronics, STHV748 Quad +/− 90 V, +/− 2 A, ⅗levels, high speed ultrasound pulser. Datasheet. Jan. 2016. 29 pages.
(Continued)

*Primary Examiner* — Katherine L Fernandez
*Assistant Examiner* — Colin T. Sakamoto
(74) *Attorney, Agent, or Firm* — Wolf, Greenfield & Sacks, P.C.

(57) ABSTRACT

A universal ultrasound device having an ultrasound includes a semiconductor die; a plurality of ultrasonic transducers integrated on the semiconductor die, the plurality of ultrasonic transducers configured to operate a first mode associated with a first frequency range and a second mode associated with a second frequency range, wherein the first frequency range is at least partially non-overlapping with the second frequency range; and control circuitry configured to: control the plurality of ultrasonic transducers to generate and/or detect ultrasound signals having frequencies in the first frequency range, in response to receiving an indication to operate the ultrasound probe in the first mode; and control the plurality of ultrasonic transducers to generate and/or detect ultrasound signals having frequencies in the second
(Continued)

frequency range, in response to receiving an indication to operate the ultrasound probe in the second mode.

26 Claims, 15 Drawing Sheets

(51) Int. Cl.
    *A61B 8/12*       (2006.01)
    *B06B 1/02*      (2006.01)
    *B06B 1/06*      (2006.01)

(52) U.S. Cl.
    CPC ........... *A61B 8/4236* (2013.01); *A61B 8/4427* (2013.01); *A61B 8/4444* (2013.01); *A61B 8/4488* (2013.01); *A61B 8/4494* (2013.01); *A61B 8/465* (2013.01); *A61B 8/467* (2013.01); *A61B 8/56* (2013.01); *B06B 1/0622* (2013.01)

(56) References Cited

U.S. PATENT DOCUMENTS

| | | | |
|---|---|---|---|
| 5,315,999 | A | 5/1994 | Kinicki et al. |
| 5,640,960 | A | 6/1997 | Jones et al. |
| 5,833,614 | A | 11/1998 | Dodd et al. |
| 5,913,823 | A | 6/1999 | Hedberg et al. |
| 6,135,963 | A | 10/2000 | Haider |
| 6,795,374 | B2 | 9/2004 | Barnes et al. |
| 6,856,175 | B2 | 2/2005 | Wodnicki |
| 7,022,074 | B2 | 4/2006 | Kristoffersen et al. |
| 7,118,531 | B2 | 10/2006 | Krill |
| 7,382,366 | B1 | 6/2008 | Klock et al. |
| 7,549,961 | B1 | 6/2009 | Hwang |
| 7,612,483 | B2 | 11/2009 | Degertekin |
| 7,615,834 | B2 | 11/2009 | Khuri-Yakub et al. |
| 7,824,335 | B2 | 11/2010 | Wodnicki |
| 7,846,102 | B2 | 12/2010 | Kupnik et al. |
| 7,892,176 | B2 | 2/2011 | Wodnicki et al. |
| 8,079,966 | B2 | 12/2011 | El-Bialy et al. |
| D657,361 | S | 4/2012 | Goodwin et al. |
| 8,147,409 | B2 | 4/2012 | Shifrin |
| 8,277,380 | B2 | 10/2012 | Daft et al. |
| 8,292,834 | B2 | 10/2012 | El-Bialy et al. |
| 8,309,428 | B2 | 11/2012 | Lemmerhirt et al. |
| 8,399,278 | B2 | 3/2013 | Lemmerhirt et al. |
| 8,852,103 | B2 | 10/2014 | Rothberg et al. |
| 9,067,779 | B1 | 6/2015 | Rothberg et al. |
| 9,229,097 | B2 | 1/2016 | Rothberg et al. |
| 9,242,275 | B2 | 1/2016 | Rothberg et al. |
| 9,275,630 | B2 | 3/2016 | Blalock et al. |
| 9,505,030 | B2 | 11/2016 | Rothberg et al. |
| 9,521,991 | B2 | 12/2016 | Rothberg et al. |
| 9,533,873 | B2 | 1/2017 | Rothberg et al. |
| 9,592,030 | B2 | 3/2017 | Rothberg et al. |
| 9,592,032 | B2 | 3/2017 | Rothberg et al. |
| 2003/0048698 | A1* | 3/2003 | Barnes ................ G01S 7/52038 367/181 |
| 2003/0097071 | A1 | 5/2003 | Halmann et al. |
| 2003/0139661 | A1 | 7/2003 | Kimchy et al. |
| 2003/0149363 | A1* | 8/2003 | Dreschel ............... A61B 8/4483 600/437 |
| 2004/0039283 | A1 | 2/2004 | Banjanin et al. |
| 2004/0254459 | A1 | 12/2004 | Kristoffersen et al. |
| 2006/0036176 | A1* | 2/2006 | Angelsen ................. A61B 8/12 600/459 |
| 2006/0173342 | A1 | 8/2006 | Panda et al. |
| 2007/0035204 | A1* | 2/2007 | Angelsen ................ B06B 1/064 310/311 |
| 2007/0232921 | A1 | 10/2007 | Lee |
| 2009/0069686 | A1 | 3/2009 | Daft et al. |
| 2009/0182237 | A1* | 7/2009 | Angelsen ............ G01S 15/8918 600/459 |
| 2009/0240148 | A1 | 9/2009 | Jeong et al. |
| 2009/0250729 | A1 | 10/2009 | Lemmerhirt et al. |
| 2010/0268081 | A1* | 10/2010 | Asafusa ................ A61B 8/4483 600/437 |
| 2011/0055447 | A1 | 3/2011 | Costa |
| 2011/0071397 | A1 | 3/2011 | Wodnicki et al. |
| 2011/0213248 | A1 | 9/2011 | Murakami et al. |
| 2011/0306886 | A1 | 12/2011 | Daft et al. |
| 2011/0319735 | A1 | 12/2011 | Hill |
| 2012/0095347 | A1* | 4/2012 | Adam ...................... A61B 8/12 600/459 |
| 2012/0194107 | A1* | 8/2012 | Kandori ................ B06B 1/0292 318/116 |
| 2012/0206014 | A1 | 8/2012 | Bibl et al. |
| 2012/0209150 | A1* | 8/2012 | Zeng ......................... A61N 7/02 601/2 |
| 2012/0215109 | A1 | 8/2012 | Kubota et al. |
| 2012/0226161 | A1 | 9/2012 | Pelissier et al. |
| 2013/0261466 | A1 | 10/2013 | Owen et al. |
| 2014/0005521 | A1 | 1/2014 | Köhler et al. |
| 2014/0117812 | A1 | 5/2014 | Hajati |
| 2014/0264660 | A1 | 9/2014 | Rothberg et al. |
| 2014/0288428 | A1* | 9/2014 | Rothberg ............... A61B 8/145 600/447 |
| 2014/0343378 | A1 | 11/2014 | Arneson et al. |
| 2015/0087991 | A1 | 3/2015 | Chen et al. |
| 2015/0257733 | A1 | 9/2015 | Corbett, III et al. |
| 2016/0007965 | A1 | 1/2016 | Murphy et al. |
| 2016/0179355 | A1 | 6/2016 | K S |
| 2016/0199030 | A1* | 7/2016 | Patil ......................... B06B 1/02 600/459 |
| 2016/0262726 | A1 | 9/2016 | Yoon et al. |
| 2016/0331353 | A1 | 11/2016 | Ralston et al. |
| 2017/0360399 | A1 | 12/2017 | Rothberg et al. |
| 2017/0360405 | A1 | 12/2017 | Rothberg et al. |
| 2017/0360413 | A1 | 12/2017 | Rothberg et al. |
| 2017/0360414 | A1 | 12/2017 | Rothberg et al. |
| 2017/0360415 | A1 | 12/2017 | Rothberg et al. |
| 2018/0070917 | A1 | 3/2018 | Rothberg et al. |
| 2019/0000418 | A1 | 1/2019 | Rothberg et al. |

OTHER PUBLICATIONS

Supertex Inc., MD1712 High Speed, Integrated Ultrasound Driver IC. Datasheet. 2012. 12 pages.
Texas Instruments, TX734 Quad Channel, 3-Level RTZ, +/− 75-V, 2-A Integrated Ultrasound Pulser. Datasheet. Nov. 2008. 6 pages.
Agarwal et al., Single-Chip Solution for Ultrasound Imaging Systems: Initial Results. 2007 IEEE Ultrasonics Symposium. Oct. 1, 2007;1563-6.
Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Kobe, Japan. Nov. 12-14, 2012;173-6.
Chen et al., Ultrasonic Imaging Transceiver Design for CMUT: A Three-Level 30-Vpp Pulse-Shaping Pulser With Improved Efficiency and a Noise-Optimized Receiver. IEEE J Solid-State Circ. Nov. 2013;48(11):2734-45.
Cheng et al., CMUT-in-CMOS ultrasonic transducer arrays with on-chip electronics. IEEE Transducers 2009. Denver, CO. Jun. 21-25, 2009;1222-5.
Daft et al., A Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;493-6.
Gurun et al., Front-end CMOS Electronics for Monolithic Integration with CMUT Arrays: Circuit Design and Initial Experimental Results. 2008 IEEE International Ultrasonics Symposium Proceedings. 2008;390-3.
Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. Doi: 10.1109/IEMBS.2010.5627580. Epub Dec. 6, 2010. 13 pages.
Kim et al., Design and Test of a Fully Controllable 64×128 2-D CMUT Array Integrated with Reconfigurable Frontend ASICs for

(56) References Cited

OTHER PUBLICATIONS

Volumetric Ultrasound Imaging. 2012 IEEE International Ultrasonics Symposium Proceedings. Oct. 7-10, 2012;77-80.

Kupnik et al., Wafer-Bonded CMUT Meets CMOS. 2010 CMOS Emerging Technology Workshop. Whistler, Canada. May 21, 2010;1-22.

Noble et al., A Cost-effective and Manufacturable Route to the Fabrication of High-Density 2D Micromachined Ultrasonic Transducer Arrays and (CMOS) Signal Conditioning Electronics on the same Silicon Substrate. 2001 IEEE Ultrasonics Symposium. 2001;941-5.

Zahorian et al., Single chip CMUT arrays with integrated CMOS electronics: Fabrication Process Development and Experimental Results. 2008 IEEE International Ultrasonics Symposium Proceedings. 2008;386-9.

International Search Report and Written Opinion dated Aug. 29, 2017 in connection with International Application No. PCT/US2017/038100.

International Search Report and Written Opinion dated Nov. 2, 2017 in connection with International Application No. PCT/US2017/049027.

Bavaro et al., Element Shape Design of 2-D CMUT Arrays for Reducing Rating Lobes. IEEE Transactions on Ultrasonics, Ferroelectrics and Frequency Control. Feb. 2008;55(2):308-18.

International Search Report and Written Opinion dated Nov. 13, 2014 in connection with International Application No. PCT/US2014/032803.

International Preliminary Report on Patentability dated Jan. 3, 2019 in connection with International Application No. PCT/US2017/038100.

Extended European Search Report dated Dec. 19, 2019 in connection with European Application No. 17815994.3.

Fairbanks et al., Ocular Ultrasound: A Quick Reference Guide ofr the On-Call Physician. EyeRounds.org. University of Iowa Carver College of Medicine posted Feb. 4, 2016. http://www.EyeRounds.org/tutorials/ultrasound.

Via et al., Lung Ultrasound in the ICU: From Diagnostic Instrument to Respiratory Monitoring Tool. Minerva Anestesiologica. Nov. 2012; 78 (11):1282-96.

Shung, Diagnostic Ultrasound: Imaging and Blood Flow Measurements. 2006; 207 pages.

\* cited by examiner

UNIVERSAL ULTRASOUND DEVICE AND RELATED APPARATUS AND METHODS

CROSS-REFERENCE TO RELATED APPLICATIONS

This Application claims the benefit under 35 U.S.C. § 119(e) of U.S. Provisional Patent Application Ser. No. 62/352,337, filed on Jun. 20, 2016, and entitled "UNIVERSAL ULTRASOUND DEVICE AND RELATED APPARATUS AND METHODS," which is hereby incorporated herein by reference in its entirety.

FIELD

The present application relates to an ultrasound device that can operate across multiple different frequency ranges to obtain high-resolution images of a subject at different depths.

BACKGROUND

Ultrasound imaging systems typically include an ultrasound probe connected to a host by an analog cable. The ultrasound probe is controlled by the host to emit and receive ultrasound signals. The received ultrasound signals are processed to generate an ultrasound image.

SUMMARY

In one embodiment, an ultrasound device includes an ultrasound probe, including a semiconductor die, and a plurality of ultrasonic transducers integrated on the semiconductor die, the plurality of ultrasonic transducers configured to operate in a first mode associated with a first frequency range and a second mode associated with a second frequency range, wherein the first frequency range is at least partially non-overlapping with the second frequency range; and control circuitry configured to: control the plurality of ultrasonic transducers to generate and/or detect ultrasound signals having frequencies in the first frequency range, in response to receiving an indication to operate the ultrasound probe in the first mode; and control the plurality of ultrasonic transducers to generate and/or detect ultrasound signals having frequencies in the second frequency range, in response to receiving an indication to operate the ultrasound probe in the second mode.

BRIEF DESCRIPTION OF THE DRAWINGS

Various aspects and embodiments of the disclosed technology will be described with reference to the following figures. It should be appreciated that the figures are not necessarily drawn to scale. Items appearing in multiple figures are indicated by the same reference number in all the figures in which they appear.

DETAILED DESCRIPTION

Figure 1A:
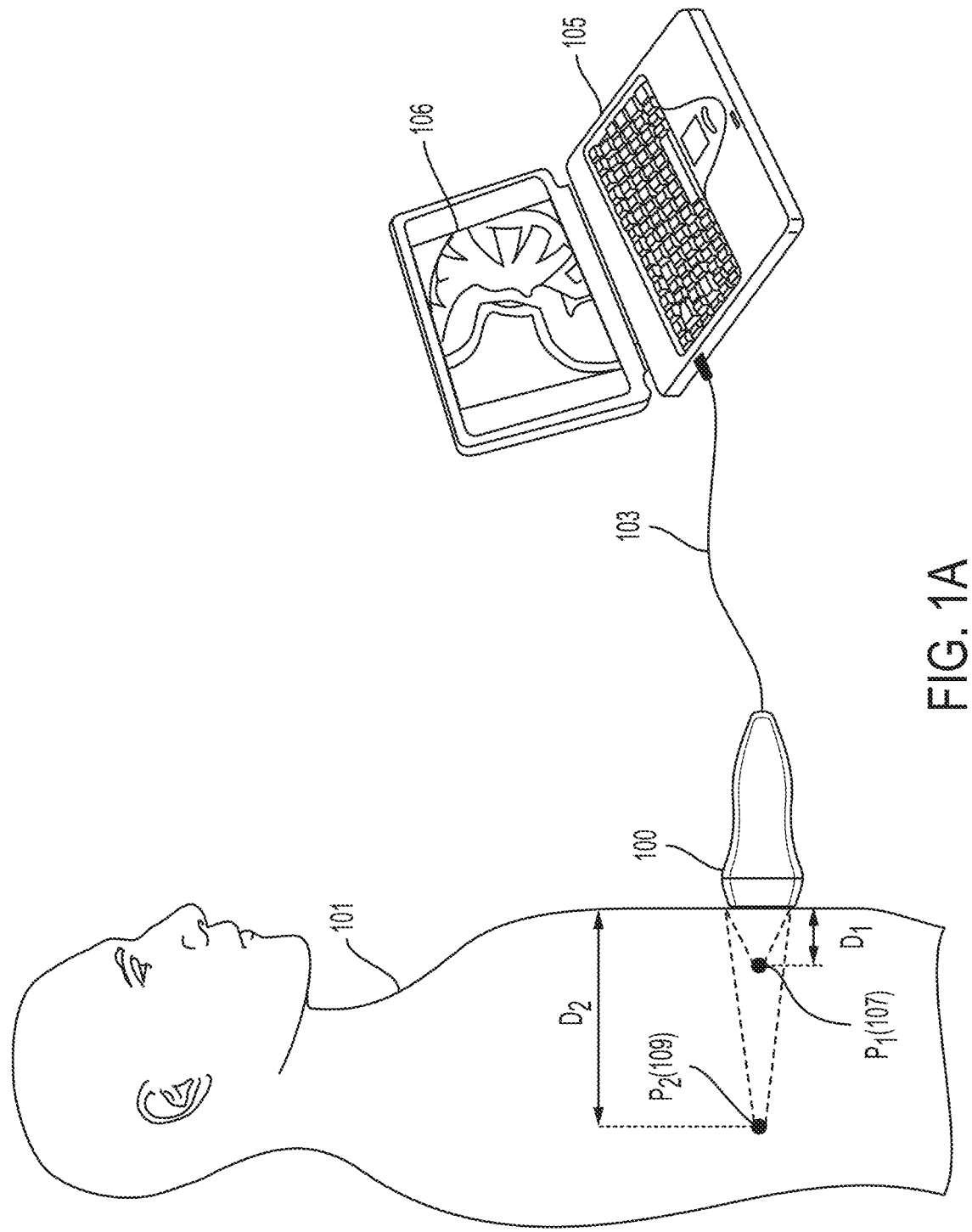
FIG. 1A is a diagram illustrating how a universal ultrasound device may be used to image a subject, in accordance with some embodiments of the technology described herein.

The present disclosure describes aspects of a "universal" ultrasound device configured to image a subject at multiple different frequency ranges. The universal ultrasound device includes multiple ultrasonic transducers at least some of which can operate at different frequency ranges, thereby enabling the use of a single ultrasound device to generate medically-relevant images of a subject at different depths. As a result, a single device (the universal ultrasound device described herein) may be used by medical professionals or other users to perform different imaging tasks that presently require use of multiple conventional ultrasound probes.

Some embodiments are directed to an ultrasound device comprising an ultrasound probe. The ultrasound probe comprises a semiconductor die; a plurality of ultrasonic transducers integrated on the semiconductor die, the plurality of ultrasonic transducers configured to operate in a first mode associated with a first frequency range and a second mode associated with a second frequency ramze, wherein the first frequency range is at least partially non-overlapping with the second frequency range; and control circuitry. The control circuitry is configured to control the plurality of ultrasonic transducers to generate and/or detect ultrasound signals having frequencies in the first frequency range, in response to receiving an indication to operate the ultrasound probe in the first mode, and control the plurality of ultrasonic transducers to generate and/or detect ultrasound signals having frequencies in the second frequency range, in response to receiving an indication to operate the ultrasound probe in the second mode.

The inventors have recognized that conventional ultrasound probes are limited because each of them operates at just a single one of several medically-relevant frequency ranges. For example, some conventional ultrasound probes operate only at frequencies in the range of 1-3 MHz (e.g., for applications such as obstetric, abdomen and gynaecological imaging), whereas other conventional probes operate only at frequencies in the range of 3-7 MHz (e.g., for applications such as breast, vascular, thyroid, and pelvic imaging). Still other conventional ultrasound probes operate only at frequencies in the range of 7-15 MHz (e.g., for applications such as musculosketal and superficial vein and mass imaging). Since higher frequency ultrasound signals attenuate faster in tissue than lower frequency ultrasound signals, conventional probes operating only at higher frequencies are used for generating images of a patient at shallow depths (e.g., 5 cm or less) for applications such as central line placement or the aforementioned imaging of superficial masses located just beneath the skin. On the other hand, conventional probes operating only at lower frequencies are used to generate images of a patient at greater depths (e.g., 10-25 cm) for applications such as cardiac and kidney imaging. As a result, a medical professional needs to use multiple different probes, which is inconvenient and expensive, as it requires procuring multiple different probes configured to operate at different frequency ranges.

By contrast, the universal ultrasound device, developed by the inventors and described herein, is configured to operate at multiple different medically-relevant frequency ranges and image patients at a sufficiently high resolution for forming medically-relevant images at a wide range of depths. As such, multiple conventional ultrasound probes can all be replaced by the single universal ultrasound device described herein, and medical professionals or other users may use a single universal ultrasound probe to perform multiple imaging tasks instead of using a multitude of conventional ultrasound probes each having limited applicability.

Figure 5A:
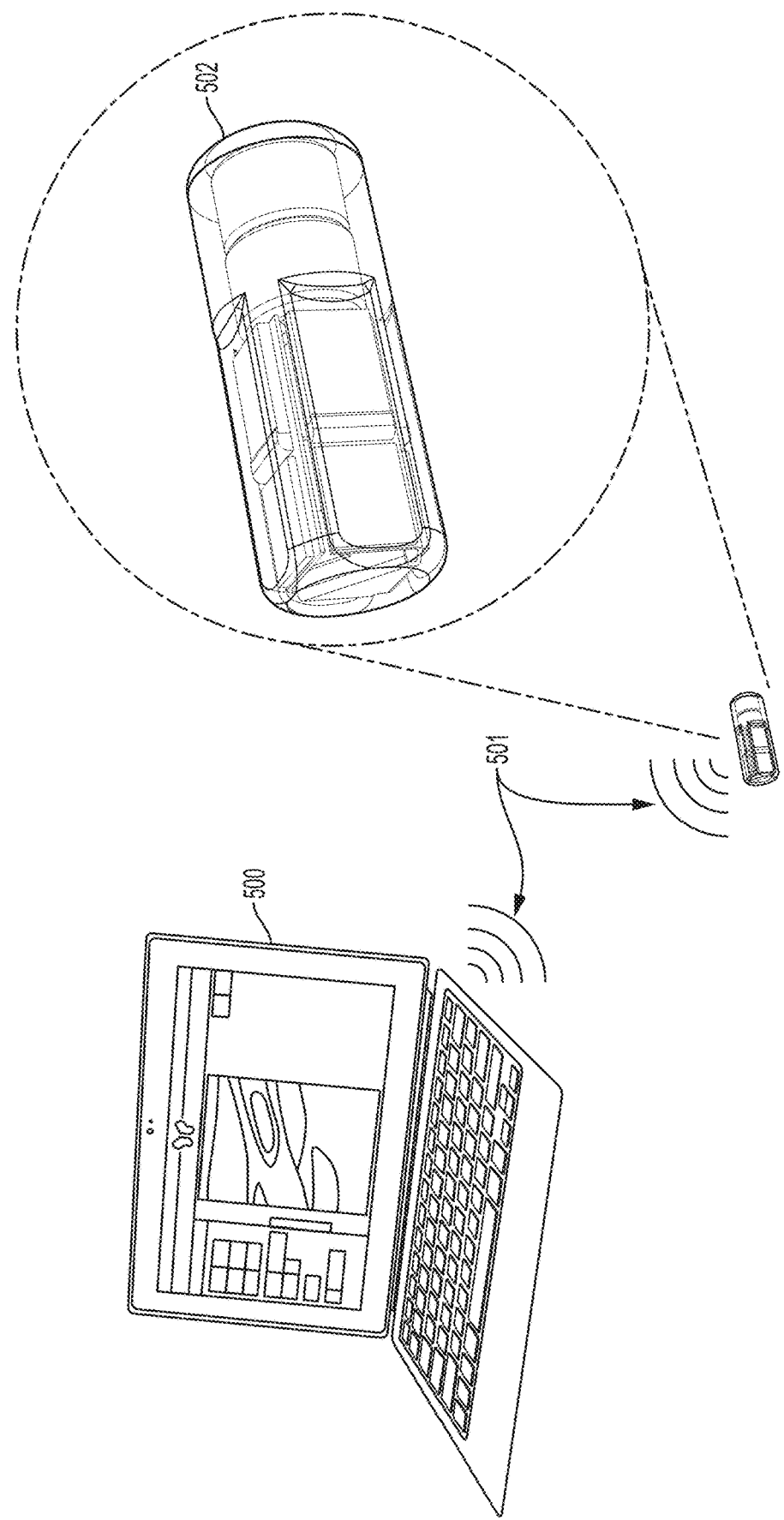
FIGS. 5A-5H illustrate a pill comprising an ultrasound probe, in accordance with some embodiments of the technology described herein.

Accordingly, some embodiments provide for wideband ultrasound probe having multiple ultrasonic transducers configured to operate in each of a multiple of modes including a first mode associated with a first frequency range and a second mode associated with a second frequency range, which is at least partially non-overlapping with the first frequency range. The multi-frequency ultrasound probe further comprises control circuitry that is configured to control the plurality of ultrasonic transducers to generate and/or detect ultrasound signals having frequencies in the first frequency range, in response to receiving an indication to operate the ultrasound probe in the first mode, and control the plurality of ultrasonic transducers to generate and/or detect ultrasound signals having frequencies in the second frequency range, in response to receiving an indication to operate the ultrasound probe in the second mode. The ultrasonic transducers may be integrated on a single substrate such as a single complementary metal oxide semiconductor (CMOS) chip, or may be on multiple chips within an ultrasound probe (e.g., as shown in FIGS. 5G and 5H).

In some embodiments, the first frequency range may include frequencies in the range of 1-5 MHz. For example, the first frequency range may be contained entirely within a range of 1-5 MHz (e.g., within a range of 2-5 MHz, 1-4 MHz, 1-3 MHz, 2-5 MHz, and/or 3-5 MHz). Accordingly, when the ultrasonic transducers of the universal ultrasound probe are operated to generate and/or detect ultrasound signals having frequencies in the first frequency range, ultrasound signals detected by the ultrasonic transducers may be used to form an image of a subject up to target depths within the subject, the target depths being in a range of 10-25 cm (e.g., within a range of 10-20 cm, 15-25 cm, 10-15 cm, 15-20 cm, and/or 20-25 cm).

In some embodiments, the second frequency range may be contained entirely within a range of 5-12 MHz (e.g., within a range of 5-10 MHz, 7-12 MHz, 5-7 MHz, 5-9 MHz, 6-8 MHz, 7-10 MHz, and/or 6-9 MHz). Accordingly, when the ultrasonic transducers of the universal ultrasound probe are operated to generate and/or detect ultrasound signals having frequencies in the second frequency range, ultrasound signals detected by the ultrasonic transducers may be used to form an image of a subject up to target depths within the subject, the target depths being in a range of 1-10 cm (e.g. within a range of 1-5 cm, 5-10 cm, 3-8 cm, 3-6 cm, and/or 3-5 cm).

In some embodiments, the multiple modes of the universal ultrasound probe in combination span at least 10 MHz or between 8-15 MHz. For this reason, a universal ultrasound probe may be sometimes called a "wideband" probe, a multi-modal probe (having multiple frequency range modes), and/or a multi-frequency probe.

It should be appreciated that a universal ultrasound probe is not limited to operating in only two modes and may operate in any suitable number of modes (e.g., 3, 4, 5, etc.) with each of the modes being associated with a respective frequency range. For example, in some embodiments, the universal ultrasound probe may operate in first, second, and third modes associated with a first, second, and third frequency ranges, respectively. The first, second, and third frequency ranges may be any suitable set of three ranges that, pairwise, do not entirely overlap one another. For example, the first frequency range may be contained entirely within a range of 1-3 MHz, the second frequency range may be contained entirely within a range of 3-7 MHz, and the third frequency range may be contained entirely within a range of 7-12 MHz. As another example, the first frequency range may be contained entirely within a range of 1-5 MHz, the second frequency range may be contained entirely within a range of 3-7 MHz, and the third frequency range may be contained entirely within a range of 5-10 MHz. In addition, each mode may also have different elevational focal regions, a feature not possible with a single 1D array using an elevational focusing acoustic lens. Each mode may also have different pitch of elements based on the frequency of operation. The different pitch may be implemented, for example, by subset selection and combinations of transducer cells.

As may be appreciated from the foregoing examples of frequency ranges, an operating mode of the ultrasound probe may be associated with a frequency bandwidth of at least 1 MHz, in some embodiments. In other embodiments, an operating mode of the ultrasound probe may be associated with a bandwidth of at least 2 MHz, at least 3 MHz, or at least 4 MHz or higher, as aspects of the technology described herein are not limited in this respect. At least some of the transducers of the ultrasound probe, and in some embodiments each transducer, ultrasonic transducer may not only operate at different frequency ranges, but also may operate in a particular frequency range (e.g., at a center frequency of the frequency range) with a wide bandwidth. In other embodiments (e.g., for Doppler imaging), an operating mode of the ultrasound prove may span bandwidths narrower than 1 MHz. As described herein, a center frequency refers to a frequency at which the resides the centroid of the intensity weighted frequencies being received.

When operating in a particular mode, ultrasonic transducers of a probe may generate ultrasound signals having the largest amount of power at a peak power frequency for the mode (e.g., which may be a center frequency of the frequency range associated with the mode). For example, when operating in a mode associated with a frequency range of 1-5 MHz, the ultrasonic transducers may be configured to generate ultrasound signals having the largest amount of power at 3 MHz. Therefore, the peak power frequency for this mode is 3 MHz in this example. As another example, when operating in a mode associated with a frequency range of 5-9 MHz, the ultrasonic transducers may be configured to generate ultrasound signals having the largest amount of power at 7 MHz, which is the peak power frequency in this example.

As may be appreciated from the foregoing examples of frequency ranges, a universal ultrasound probe may be configured to operate in multiple modes including a first mode associated with a first frequency range having a first peak power frequency and a second mode associated with as second frequency range having a second peak power frequency. In some instances, the difference between the first and second peak power frequencies is at least a threshold amount (e.g., at least 1 MHz, at least 2 MHz, at least 3 MHz, at least 4 MHz, at least 5 MHz, etc.).

It should be appreciated that, when operating in a frequency range, an ultrasonic transducer may, in some embodiments, generate signals at frequencies outside of the operating frequency range. However, such signals would be generated at less than a fraction (e.g., ½, ⅓, ⅕, etc.) of the largest power at which a signal at a center frequency of the range is generated, for example 6 dB down from the maximum power.

The universal ultrasound probe described herein may be used for a broad range of medical imaging tasks including, but not limited to, imaging a patient's liver, kidney, heart, bladder, thyroid, carotid artery, lower venous extremity, and performing central line placement. Multiple conventional ultrasound probes would have to be used to perform all these imaging tasks. By contrast, a single universal ultrasound probe may be used to perform all these tasks by operating, for each task, at a frequency range appropriate for the task, as shown in Table 1 together with corresponding depths at which the subject is being imaged.

TABLE 1

Illustrative depths and frequencies at which a universal ultrasound probe implemented in accordance with embodiments described herein can image a subject.

| Organ | Frequencies | Depth (up to) |
| --- | --- | --- |
| Liver/Right Kidney | 2-5 MHz | 15-20 cm |
| Cardiac (adult) | 1-5 MHz | 20 cm |
| Bladder | 2-5 MHz; 3-6 MHz | 10-15 cm; 5-10 cm |
| Lower extremity venous | 4-7 MHz | 4-6 cm |
| Thyroid | 7-12 MHz | 4 cm |
| Carotid | 5-10 MHz | 4 cm |
| Central Line Placement | 5-10 MHz | 4 cm |

FIG. 1A further illustrates how a universal ultrasound probe may operate in different modes, associated with different frequency ranges, to image a subject at different depths. As shown in FIG. 1A, ultrasound probe 100 is being used to image subject 101. When operating in a first mode, associated with a first frequency range (e.g., 1-3 MHz), the ultrasonic transducers in probe 100 may be configured to image the subject at or about a point 109, also labeled $P_2$, located at a depth $D_2$ (e.g., 15-20 cm) from the subject's skin. When operating in a second mode, associated with a second frequency range (e.g., 6-8 MHz), the ultrasonic transducers in probe 100 may be configured to image the subject at or about a point 107, also labeled $P_1$, located at a depth $D_1$ (e.g., 1-5 cm) from the subject's skin. In some embodiments, the distance D2 is greater than the distance D1 by at least a threshold distance (e.g., at least 5 cm, at least 7 cm, between 3 and 7 cm, or any range or number within such ranges).

Ultrasound probe 100 transmit may be configured to transmit data collected by the probe 100 to one or more external devices for further processing. For example, as shown in FIG. 1A, ultrasound probe 100 may be configured to transmit data collected by probe 100 via wired connection 103 to computing device 105 (a laptop in this non-limiting example), which may process the data to generate and display an image 111 of the subject 101 on a display.

Various factors contribute to the ability of the universal ultrasound probe to operate in multiple modes associated with different and medically-relevant frequency ranges. One such factor is that the ultrasonic transducers may be formed by capacitive micromachined ultrasonic transducers (CMUTs) and, in some embodiments, at least some (and in some embodiments each) of multiple ultrasonic transducers in the universal ultrasound probe is configured to operate in collapsed mode and in non-collapsed mode. As described herein, a "collapsed mode" refers to a mode of operation in which at least one portion of a CMUT ultrasonic transducer membrane is mechanically fixed and at least one portion of the membrane is free to vibrate based on a changing voltage differential between the electrode and the membrane. When operating in collapsed mode, a CMUT ultrasonic transducer is capable of generating more power at higher frequencies. Switching operation of multiple ultrasonic transducers from non-collapsed mode into collapsed mode (and vice versa) allows the ultrasound probe to change the frequency range at which the highest power ultrasound signals are being emitted.

Accordingly, in some embodiments, an ultrasound probe operates in a first mode associated with a first frequency range (e.g., 1-5 MHz, with a peak power frequency of 3 MHz) by operating its transducers in non-collapsed mode, and operates in a second mode associated with a second frequency range (e.g., 5-9 MHz, with a peak power frequency of 7 MHz) by operating its transducers in collapsed mode. In some embodiments, the ultrasound probe includes control circuitry (e.g., circuitry 108 shown in FIG. 1B) configured to control the probe to operate in either first mode or the second mode and, to this end, may apply appropriate voltages to the ultrasonic transducers to cause them to operate in collapsed mode or in non-collapsed mode. For example, in some embodiments, the control circuitry is configured to cause ultrasonic transducers in the probe to operate in collapsed mode by applying a voltage to the transducers that exceeds a threshold voltage, which is sometimes called a "collapse" voltage. The collapse voltage may be in the range of 30-110 Volts and, in some embodiments, may be approximately 50 Volts. It should be noted that, while in some embodiments operating a probe's transducers in collapsed and non-collapsed modes may be a factor that helps the probe to operate in multiple frequency range modes, there may also be other factors that allow the probe to do so (e.g., an analog receiver capable of broadband signal amplification of about 1-1.5 MHz).

Another factor that contributes to the ability of the universal ultrasound probe to operate in multiple modes associated with different and medically-relevant frequency ranges is that the ultrasonic transducers may be arranged in an array having a pitch adequate for both high-frequency and low frequency scanning. For example, in some embodiments, at least some of the ultrasonic transducers may be spaced apart from its nearest neighbor at a distance less than half of a wavelength corresponding to the highest frequency at which the probe is designed to operate to reduce (e.g., eliminate) aliasing effects. Each mode may also have different pitch of elements based on the frequency of operation. The different pitch is enabled by subset selection and combining of CUT cells. Adequate pitches for a frequency are generally spaced between about λ and λ/4, where λ is the wavelength at the specified frequency. Exemplary pitches may include, but are not limited to, 500 microns (μm) (very low frequencies), 200 μm (moderate frequencies), and 125 μm (high frequencies). Also, in certain embodiments, pitches may be made wider due to element directivity helping to suppress aliasing artifacts (e.g., on the order of λ).

Another factor that contributes to the ability of the universal ultrasound probe to operate in multiple triodes associated with different and medically-relevant frequency ranges is that the ultrasound transducers may be arranged in an array having an aperture (determined by the width and height of the array) that allows for both shallow and deep scans to be performed. For example, each mode may have a different active aperture. The total aperture accommodates the largest field-of-view needed to cover the application space of any one probe. Examples include all combinations of 1 cm, 2 cm, 3 cm, 4 cm, 5 cm in the azimuth direction and 1 cm, 2 cm, 3 cm, 4 cm, 5 cm in the elevation direction.

Another factor that contributes to the ability of the universal ultrasound probe to operate in multiple modes associated with different and medically-relevant frequency ranges is the selection of a CUT cell size. Grouping CUT cells together increases both directivity and sensitivity. In addition, directivity increases with frequency as the element remains fixed in size. Thus, grouping CUT cells together for lower frequencies can be balanced with less grouping for higher frequencies to maintain a consistent directivity.

Another factor that contributes to the ability of the universal ultrasound probe to operate in multiple modes associated with different and medically-relevant frequency ranges is that, in addition to being capable of operating in multiple frequency ranges, ultrasonic transducers in the probe are capable of generating low-frequency and high-frequency acoustic waveforms having a broad bandwidth (e.g., at least 100 KHz, at least 500 KHz, at least 1 MHz, at least 2 MHz, at least 5 MHz, at least 7 MHz, at least 15 MHz, at least 20 MHz, etc.).

Another factor that contributes to the ability of the universal ultrasound probe to operate in multiple modes associated with different and medically-relevant frequency ranges is that, in some embodiments, the probe may include programmable delay mesh circuitry that allows for transmit beamforming to focus at multiple depths, including depths in the range of 2-35 cm. Programmable delay mesh circuitry is further described in U.S. Pat. No. 9,229,097, assigned to the assignee of the present application, the contents of which are incorporated by reference herein in their entirety.

Still another factor that contributes to the ability of the universal ultrasound probe to operate in multiple modes associated with different and medically-relevant frequency ranges is that, in some embodiments, the probe may include circuitry that allows for receive beamforming to focus at multiple depths, including depths in the range of 2-35 cm.

In one exemplary embodiment, a universal ultrasound probe may include an array of 576×256 ultrasonic transducers, spaced at a pitch of 52 μm, and having an array aperture of about 3 cm×1.33 cm. At least some of the transducers can operate in a frequency range of 1-15 MHz with a bandwidth of 0.1-12 MHz. In a another exemplary embodiment, a universal ultrasound probe may include an array of 64×140 transducers spaced at 208 μm, and having an array aperture of about 3 cm×1.33 cm, operating in a frequency range of 1.5-5 MHz, and from 5-12 MHz.

In some embodiments, a universal ultrasound probe (e.g., probe 100) may be implemented in any of numerous physical configurations, and has the capabilities incorporated to perform imaging in modes as may be used when imaging with two or more of the following: a linear probe, a sector probe, a phased array probe, a curvilinear probe, a convex probe, and/or a 3D imaging probe. Additionally, in some embodiments, the ultrasound probe may be embodied in a hand-held device. The hand-held device may include a screen to display obtained images (e.g., as shown in FIGS. 6A-6B). Additionally or alternatively, the hand-held device may be configured to transmit (via a wireless or a wired connection) data to an external device for further processing (e.g., to form one or more ultrasound images). As another example, in some embodiments, the ultrasound probe may be embodied in a pill (e.g., as shown in FIGS. 5A-5H) to be swallowed by a subject and configured to image the subject as it is traveling through his/her digestive system. As another example, in some embodiments, the ultrasound probe may be embodied in a patch configured to be affixed to the subject (e.g., as shown in FIGS. 6C-6E).

The aspects and embodiments described above, as well as additional aspects and embodiments, are described further below. These aspects and/or embodiments may be used individually, all together, or in any combination of two or more, as the technology described herein is not limited in this respect.

Figure 1B:
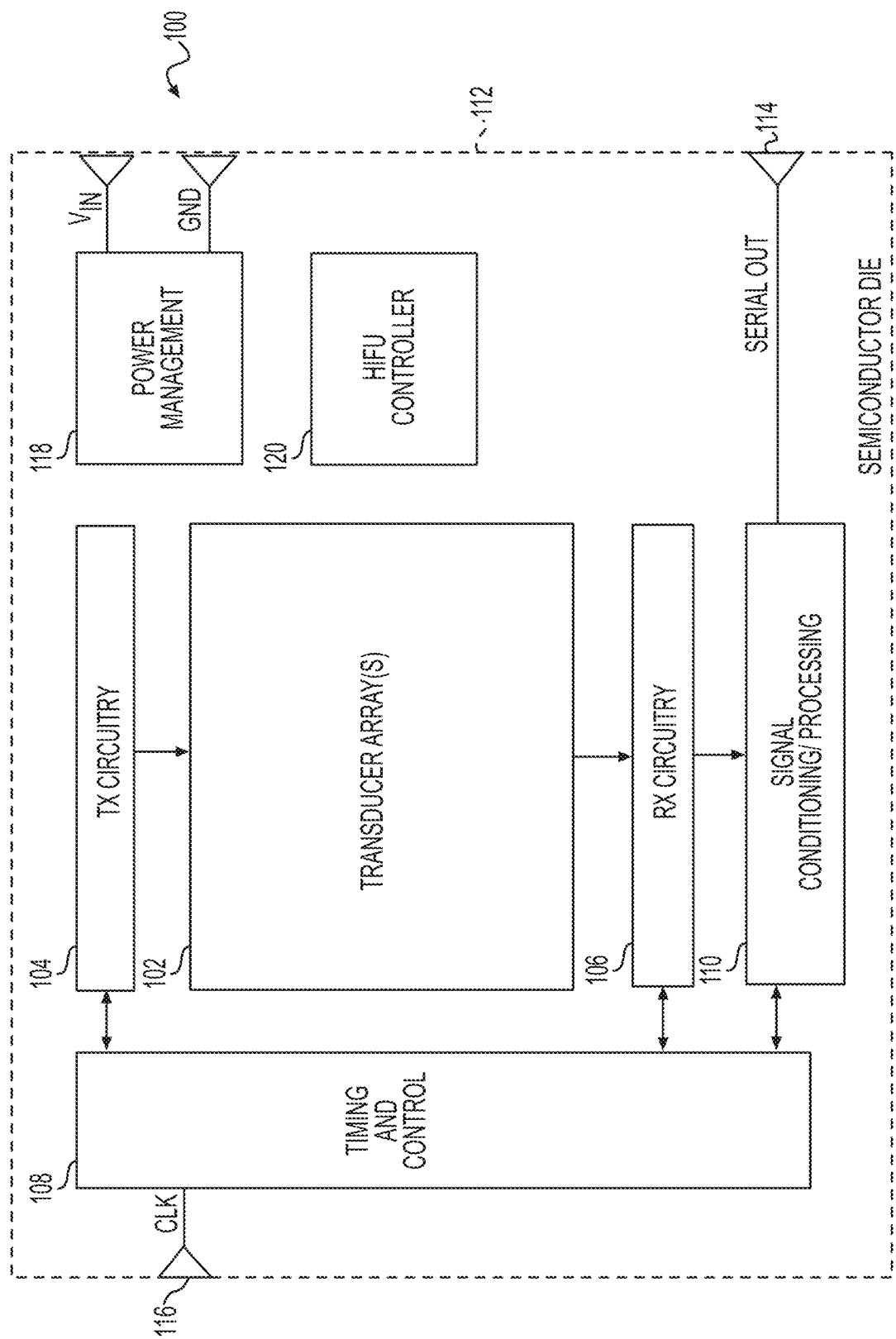
FIG. 1B is a block diagram of an illustrative example of a universal ultrasound device, in accordance with some embodiments of the technology described herein.

FIG. 1B shows an illustrative example of a monolithic ultrasound device 100 embodying various aspects of the technology described herein. As shown, the device 100 may include one or more transducer arrangements (e.g., arrays) 102, transmit (TX) circuitry 104, receive (RX) circuitry 106, a timing & control circuit 108, a signal conditioning/processing circuit 110, a power management circuit 118, and/or a high-intensity focused ultrasound (HIFU) controller 120. In the embodiment shown, all of the illustrated elements are formed on a single semiconductor die 112. It should be appreciated, however, that in alternative embodiments one or more of the illustrated elements may be instead located off-chip. In addition, although the illustrated example shows both TX circuitry 104 and RX circuitry 106, in alternative embodiments only TX circuitry or only RX circuitry may be employed. For example, such embodiments may be employed in a circumstance where one or more transmission-only devices 100 are used to transmit acoustic signals and one or more reception-only devices 100 are used to receive acoustic signals that have been transmitted through or reflected off of a subject being ultrasonically imaged.

It should be appreciated that communication between one or more of the illustrated components may be performed in any of numerous ways. In some embodiments, for example, one or more high-speed busses (not shown), such as that employed by a unified. Northbridge, may be used to allow high-speed intra-chip communication or communication with one or more off-chip components.

The one or more transducer arrays 102 may take on any of numerous forms, and aspects of the present technology do not necessarily require the use of any particular type or arrangement of transducer cells or transducer elements. Indeed, although the term "array" is used in this description, it should be appreciated that in some embodiments the transducer elements may not be organized in an array and may instead be arranged in some non-array fashion. In various embodiments, each of the transducer elements in the array 102 may, for example, include one or more capacitive micromachined ultrasonic transducers (CMUTs), one or more CMOS ultrasonic transducers (CUTS), one or more piezoelectric micromachined ultrasonic transducers (PMUTs), and/or one or more other suitable ultrasonic transducer cells. In some embodiments, the transducer elements of the transducer array 102 may be formed on the same chip as the electronics of the TX circuitry 104 and/or RX circuitry 106 or, alternatively integrated onto the chip having the TX circuitry 104 and/or RX circuitry 106. In still other embodiments, the transducer elements of the transducer array 102, the TX circuitry 104 and/or RX circuitry 106 may be tiled on multiple chips.

The transducer arrays 102, TX circuitry 104, and RX circuitry 106 may be, in some embodiments, integrated in a single ultrasound probe. In some embodiments, the single ultrasound probe may be a hand-held probe including, but not limited to, the hand-held probes described below with reference to FIGS. 6A, 6B, and 7. In other embodiments, the single ultrasound probe may be embodied in a patch that may be coupled to a patient. FIGS. 6C and 6D provide a non-limiting illustration of such a patch. The patch may be configured to transmit, wirelessly, data collected by the patch to one or more external devices for further processing. In other embodiments, the single ultrasound probe may be embodied in a pill that may be swallowed by a patient. The pill may be configured to transmit, wirelessly, data collected by the ultrasound probe within the pill to one or more external devices for further processing. FIGS. 5A-5H illustrate non-limiting examples of such a pill.

A CUT may include, for example, a cavity formed in a CMOS wafer, with a membrane overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasonic transducer cell and integrated circuit on a single substrate (the CMOS wafer). Such embodiments are further described with reference to FIG. 4 below, and additional information regarding microfabricated ultrasonic transducers may also be found in U.S. Pat. No. 9,067,779, assigned to the assignee of the present application, the contents of which are incorporated by reference herein in their entirety.

The TX circuitry 104 (if included) may, for example, generate pulses that drive the individual elements of, or one or more groups of elements within, the transducer array(s) 102 so as to generate acoustic signals to be used for imaging. The RX circuitry 106, on the other hand, may receive and process electronic signals generated by the individual elements of the transducer array(s) 102 when acoustic signals impinge upon such elements.

In some embodiments, the timing & control circuit 108 may be, for example, responsible for generating all timing and control signals that are used to synchronize and coordinate the operation of the other elements in the device 100. In the example shown, the timing & control circuit 108 is driven by a single clock signal CLK supplied to an input port 116. The clock signal CLK may be, for example, a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 1) in the signal conditioning/processing circuit 110, or a 20 Mhz, 40 MHz, 100 MHz or 200 MHz clock used to drive other digital components on the die 112, and the timing & control circuit 108 may divide or multiply the clock CLK, as necessary, to drive other components on the die 112. In other embodiments, two or more clocks of different frequencies (such as those referenced above) may be separately supplied to the timing & control circuit 108 from an off-chip source.

The power management circuit 118 may be, for example, responsible for converting one or more input voltages $V_{IN}$ from an off-chip source into voltages needed to carry out operation of the chip, and for otherwise managing power consumption within the device 100. In some embodiments, for example, a single voltage (e.g., 1.5 V, 5V, 12V, 80V, 100V, 120V, etc.) may be supplied to the chip and the power management circuit 118 may step that voltage up or down, as necessary, using a charge pump circuit or via some other DC-to-DC voltage conversion mechanism. In other embodiments, multiple different voltages may be supplied separately to the power management circuit 118 for processing and/or distribution to the other on-chip components.

As shown in FIG. 1B, in some embodiments, a HIFU controller 120 may be integrated on the die 112 so as to enable the generation of HIFU signals via one or more elements of the transducer array(s) 102. In other embodiments, a HIFU controller for driving the transducer array(s) 102 may be located off-chip, or even within a device separate from the device 100. That is, aspects of the present disclosure relate to provision of ultrasound-on-a-chip HIFU systems, with and without ultrasound imaging capability. It should be appreciated, however, that some embodiments may not have any HIFU capabilities and thus may not include a HIFU controller 120.

Moreover, it should be appreciated that the HIFU controller 120 may not represent distinct circuitry in those embodiments providing HIFU functionality. For example, in some embodiments, the remaining circuitry of FIG. 1B (other than the HIFU controller 120) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage level) appropriate for imaging applications may cause the system to operate as an imaging system, whereas providing a higher power level (or voltage level) may cause the system to operate for HIFU. Such power management may be provided by off-chip control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-chip circuitry may be utilized to provide both functions, with suitable timing sequences used to control the operation between the two modalities.

In the example shown, one or more output ports 114 may output a high-speed serial data stream generated by one or more components of the signal conditioning/processing circuit 110. Such data streams may be, for example, generated by one or more USB 2.0, 3.0 and 3.1 modules, and/or one or more 10 GB/s, 40 GB/s, or 100 GB/s Ethernet modules, integrated on the die 112. In some embodiments, the signal stream produced on output port 114 can be fed to a computer, tablet, or smartphone for the generation and/or display of 2-dimensional, 3-dimensional, and/or tomographic images. In embodiments in which image formation capabilities are incorporated in the signal conditioning/processing circuit 110, even relatively low-power devices, such as smartphones or tablets which have only a limited amount of processing power and memory available for application execution, can display images using only a serial data stream from the output port 114. As noted above, the use of on-chip analog-to-digital conversion and a high-speed serial data link to offload a digital data stream is one of the features that helps facilitate an "ultrasound on a chip" solution according to some embodiments of the technology described herein.

Devices 100 such as that shown in FIGS. 1A and 1B may be used in any of a number of imaging and/or treatment (e.g., HIFU) applications, and the particular examples discussed herein should not be viewed as limiting. In one illustrative implementation, for example, an imaging device including an N×M planar or substantially planar array of CMUT elements may itself be used to acquire an ultrasonic image of a subject, e.g., a person's abdomen, by energizing some or all of the elements in the array(s) 102 (either together or individually) during one or more transmit phases, and receiving and processing signals generated by some or all of the elements in the array(s) 102 during one or more receive phases, such that during each receive phase the CMUT elements sense acoustic signals reflected by the subject. In other implementations, some of the elements in the array(s) 102 may be used only to transmit acoustic signals and other elements in the same array(s) 102 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single device 100 or on a single die 112.

Transmit and Receive Circuit

Figure 2:
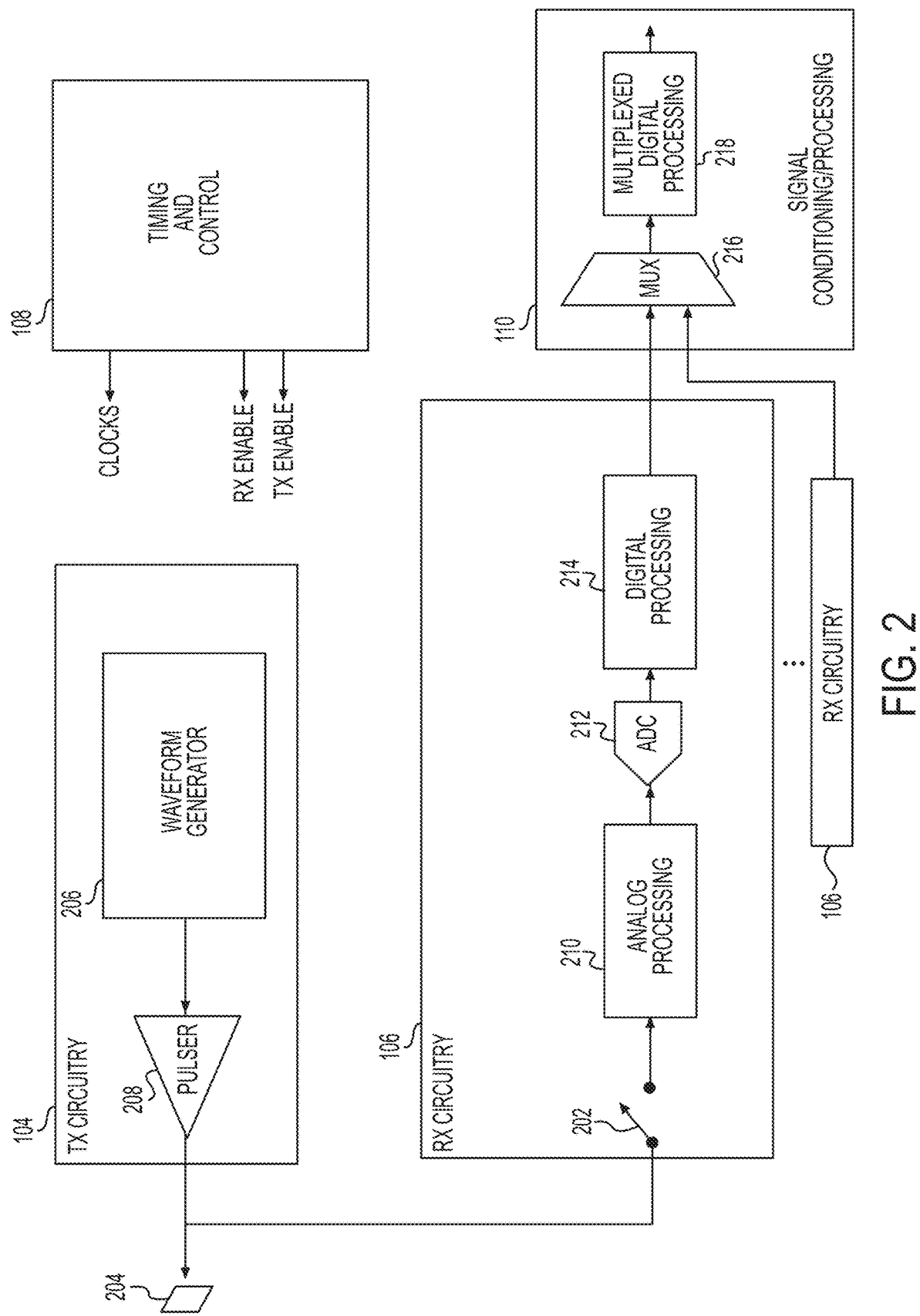
FIG. 2 is a block diagram illustrating how, in some embodiments, the transmit (TX) circuitry and the receive (RX) circuitry for a given transducer element of a universal ultrasound device may be used either to energize the element to emit an ultrasonic pulse, or to receive and process a signal from the element representing an ultrasonic pulse sensed by the transducer element, in accordance with some embodiments of the technology described herein.

FIG. 2 is a block diagram illustrating how, in some embodiments, the TX circuitry 104 and the RX circuitry 106 for a given transducer element 204 may be used either to energize the transducer element 204 to emit an ultrasonic pulse, or to receive and process a signal from the transducer element 204 representing an ultrasonic pulse sensed by it. In some implementations, the TX circuitry 104 may be used during a "transmission" phase, and the RX circuitry may be used during a "reception" phase that is non-overlapping with the transmission phase. As noted above, in some embodiments, a device 100 may alternatively employ only TX circuitry 104 or only RX circuitry 106, and aspects of the present technology do not necessarily require the presence of both such types of circuitry. In various embodiments, TX circuitry 104 and/or RX circuitry 106 may include a TX circuit and/or an RX circuit associated with a single transducer cell (e.g., a CUT or CMUT), a group of two or more transducer cells within a single transducer element 204, a single transducer element 204 comprising a group of transducer cells, a group of two or more transducer elements 204 within an array 102, or an entire array 102 of transducer elements 204.

In the example shown in FIG. 2, the TX circuitry 104/RX circuitry 106 includes a separate TX circuit and a separate RX circuit for each transducer element 204 in the array(s) 102, but there is only one instance of each of the tinting & control circuit 108 and the signal conditioning/processing circuit 110. Accordingly, in such an implementation, the timing & control circuit 108 may be responsible for synchronizing and coordinating the operation of all of the TX circuitry 104/RX circuitry 106 combinations on the die 112, and the signal conditioning/processing circuit 110 may be responsible for handling inputs from all of the RX circuitry 106 on the die 112. In other embodiments, timing and control circuit 108 may be replicated for each transducer element 204 or for a group of transducer elements 204.

As shown in FIG. 2, in addition to generating and/or distributing clock signals to drive the various digital components in the device 100, the timing & control circuit 108 may output either an "TX enable" signal to enable the operation of each TX circuit of the TX circuitry 104, or an "RX enable" signal to enable operation of each RX circuit of the RX circuitry 106. In the example shown, a switch 202 in the RX circuitry 106 may always be opened during the TX circuitry 104 is enabled, so as to prevent an output of the TX circuitry 104 from driving the RX circuitry 106. The switch 202 may be closed when operation of the RX circuitry 106 is enabled, so as to allow the RX circuitry 106 to receive and process a signal generated by the transducer element 204.

As shown, the TX circuitry 104 for a respective transducer element 204 may include both a waveform generator 206 and a pulser 208. The waveform generator 206 may, for example, be responsible for generating a waveform that is to be applied to the pulser 208, so as to cause the pulser 208 to output a driving signal to the transducer element 204 corresponding to the generated waveform.

In the example shown in FIG. 2, the RX circuitry 106 for a respective transducer element 204 includes an analog processing block 210, art analog-to-digital converter (ADC) 212, and a digital processing block 214. The ADC 212 may, for example, comprise an 8-bit, 10-bit, 12-bit or 14-bit, and 5 MHz, 20 MHz, 25 MHz, 40 MHz, 50 MHz, or 80 MHz ADC. The ADC timing may be adjusted to nm at sample rates corresponding to the mode based needs of the application frequencies. For example, a 1.5 MHz acoustic signal may be detected with a setting of 20 MHz. The choice of a higher vs. lower ADC rate provides a balance between sensitivity and power vs. lower data rates and reduced power, respectively. Therefore, lower ADC rates facilitate faster pulse repetition frequencies, increasing the acquisition rate in a specific mode.

After undergoing processing in the digital processing block 214, the outputs of all of the RX circuits on the die 112 (the number of which, in this example, is equal to the number of transducer elements 204 on the chip) are fed to a multiplexer (MUX) 216 in the signal conditioning/processing circuit 110. In other embodiments, the number of transducer elements is larger than the number of RX circuits, and several transducer elements provide signals to a single RX circuit. The MUX 216 multiplexes the digital data from the RX circuits, and the output of the MUX 216 is fed to a multiplexed digital processing block 218 in the signal conditioning/processing circuit 110, for final processing before the data is output from the die 112, e.g., via one or more high-speed serial output ports 114. The MUX 216 is optional, and in some embodiments parallel signal processing is performed. A high-speed serial data port may be provided at any interface between or within blocks, any interface between chips and/or any interface to a host. Various components in the analog processing block 210 and/or the digital processing block 214 may reduce the amount of data that needs to be output from the die 112 via a high-speed serial data link or otherwise. In some embodiments, for example, one or more components in the analog processing block 210 and/or the digital processing block 214 may thus serve to allow the RX circuitry 106 to receive transmitted and/or scattered ultrasound pressure waves with an improved signal-to-noise ratio (SNR) and in a manner compatible with a diversity of waveforms. The inclusion of such elements may thus further facilitate and/or enhance the disclosed "ultrasound-on-a-chip" solution in some embodiments.

Although particular components that may optionally be included in the analog processing block 210 are described below, it should be appreciated that digital counterparts to such analog components may additionally or alternatively be employed in the digital processing block 214. The converse is also true. That is, although particular components that may optionally be included in the digital processing block 214 are described below, it should be appreciated that analog counterparts to such digital components may additionally or alternatively be employed in the analog processing block 210.

Layout of Ultrasonic Transducers

Figure 3:
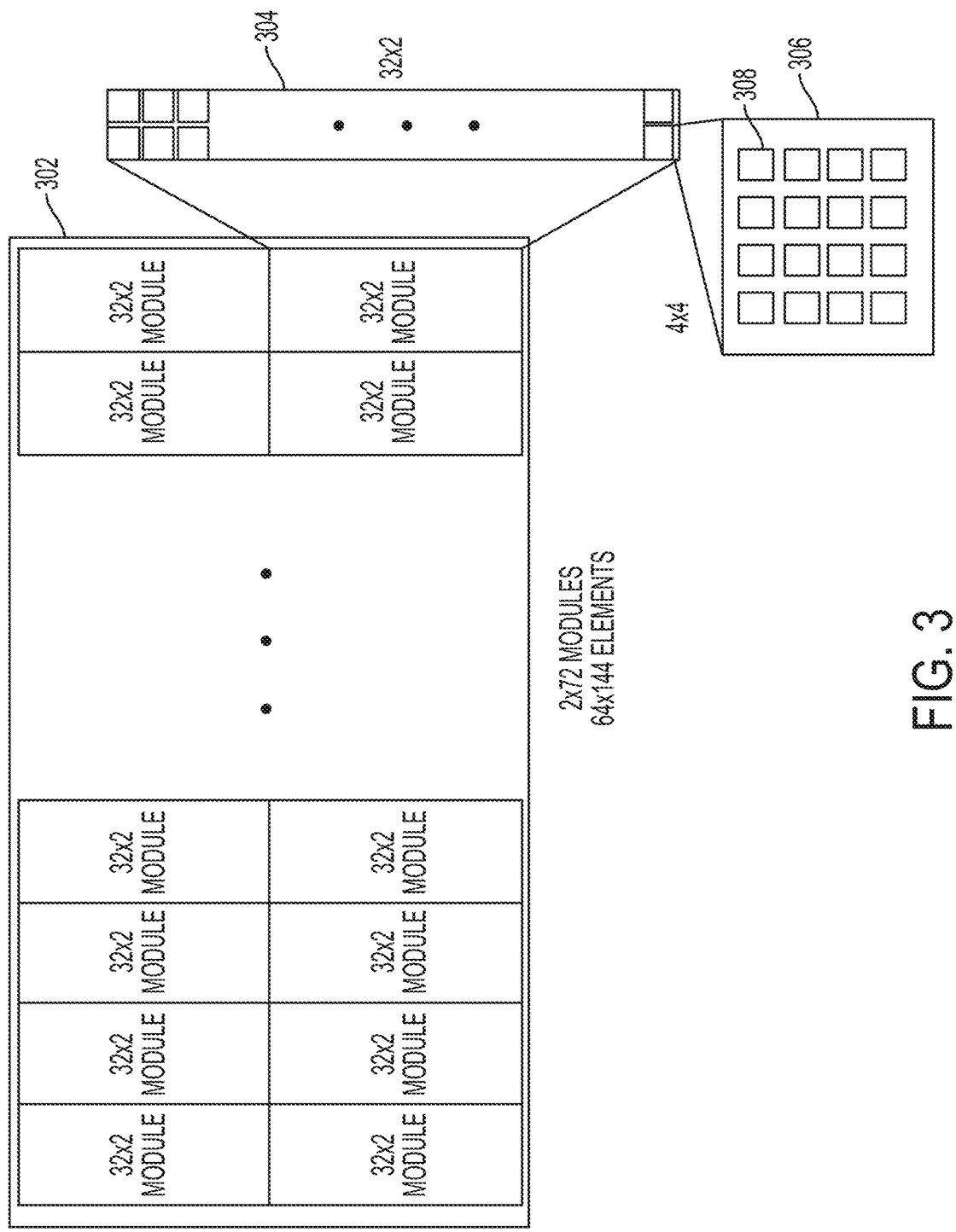
FIG. 3 shows an illustrative arrangement of ultrasonic transducers integrated with the substrate of a universal ultrasound device, in accordance with some embodiments of the technology described herein.

FIG. 3 shows substrate 302 (e.g., a semiconductor die) of an ultrasound device having multiple ultrasound circuitry modules 304 formed thereon. As shown, an ultrasound circuitry module 304 may comprise multiple ultrasound elements 306. An ultrasound element 306 may comprise multiple ultrasonic transducers 308, sometimes termed ultrasonic transducers.

In the illustrated embodiment, substrate 302 comprises 144 modules arranged as an array having two rows and 72 columns. However, it should be appreciated that a substrate of a single substrate ultrasound device may comprise any suitable number of ultrasound circuitry modules (e.g., at least two modules, at least ten modules, at least 100 modules, at least 1000 modules, at least 5000 modules, at least 10,000 modules, at least 25,000 modules, at least 50,000 modules, at least 100,000 modules, at least 250,000 modules, at least 500,000 modules, between two and a million modules, or any number or range of numbers within such ranges) that may be arranged as an two-dimensional array of modules having any suitable number of rows and columns or in any other suitable way.

In the illustrated embodiment, each ultrasound circuitry module 304 comprises 64 ultrasound elements arranged as an array having 32 rows and two columns. However, it should be appreciated that an ultrasound circuitry module may comprise any suitable number of ultrasound elements (e.g., one ultrasound element, at least two ultrasound elements, at least four ultrasound elements, at least eight ultrasound elements, at least 16 ultrasound elements, at least 32 ultrasound elements, at least 64 ultrasound elements, at least 128 ultrasound elements, at least 256 ultrasound elements, at least 512 ultrasound elements, between two and 1024 elements, at least 2500 elements, at least 5,000 elements, at least 10,000 elements, at least 20,000 elements, between 1000 and 20,000 elements, or any number or range of numbers within such ranges) that may be arranged as a two-dimensional array of ultrasound elements having any suitable number of rows and columns or in any other suitable way.

In the illustrated embodiment, each ultrasound element 306 comprises 16 ultrasonic transducers arranged as a two-dimensional array having four rows and four columns. However, it should be appreciated that an ultrasound element may comprise any suitable number and/or groupings of ultrasonic transducer cells (e.g., one, at least two, four, at least four, 9, at least 9, at least 16, 25, at least 25, at least 36, at least 49, at least 64, at least 81, at least 100, between one and 200, or any number or range of numbers within such ranges) that may be arranged as a two dimensional array having any suitable number of rows and columns (square or rectangular) or in any other suitable way. In addition, the transducer cells may include shapes such as circular, oval, square or other polygons, for example.

It should be appreciated that any of the components described above (e.g., ultrasound transmission units, ultrasound elements, ultrasonic transducers) may be arranged as a one-dimensional array, as a two-dimensional array, or in any other suitable manner.

In some embodiments, an ultrasound circuitry module may comprise circuitry in addition to one or more ultrasound elements. For example, an ultrasound circuitry module may comprise one or more waveform generators and/or any other suitable circuitry.

In some embodiments, module interconnection circuitry may be integrated with the substrate 302 and configured to connect ultrasound circuitry modules to one another to allow data to flow among the ultrasound circuitry modules. For example, the device module interconnection circuitry may provide for connectivity among adjacent ultrasound circuitry modules. In this way, an ultrasound circuitry module may be configured to provide data to and/or received data from one or more other ultrasound circuitry modules on the device.

Ultrasonic Transducers

The ultrasonic transducers of a universal ultrasound probe may be formed in any of numerous ways and, in some embodiments, may be formed as described with reference to FIG. 4.

Figure 4:
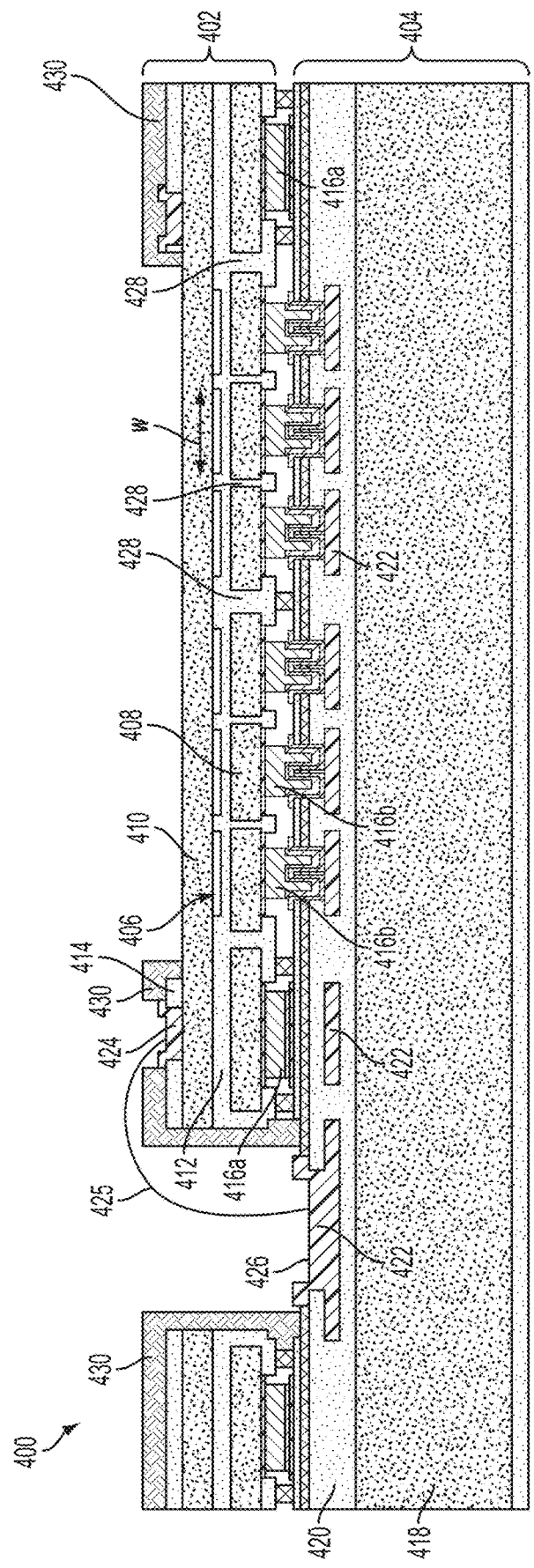
FIG. 4 is a cross-sectional view of a device including a CMOS wafer integrated with a substrate having sealed cavities, in accordance with some embodiments of the technology described herein.

FIG. 4 is a cross-sectional view of an ultrasound device including a CMOS wafer integrated with an engineered substrate having sealed cavities, according to a non-limiting embodiment of the present application. The device 400 may be formed in any suitable way and, for example, by implementing the methods described in the aforementioned U.S. Pat. No. 9,067,779.

The device 400 includes an engineered substrate 402 integrated with a CMOS wafer 401. The engineered substrate 402 includes a plurality of cavities 406 formed between a first silicon device layer 408 and a second silicon device layer 410. A silicon oxide ($SiO_2$) layer 412 (e.g., a thermal silicon oxide—a silicon oxide formed by thermal oxidation of silicon) may be formed between the first and second silicon device layers 408 and 410, with the cavities 406 being formed therein. In this non-limiting example, the first silicon device layer 408 may be configured as a bottom electrode and the second silicon device layer 410 may be configured as a membrane. Thus, the combination of the first silicon device layer 408, second silicon device layer 410, and cavities 406 may form an ultrasonic transducer (e.g., a CMUT), of which six are illustrated in this non-limiting cross-sectional view. To facilitate operation as a bottom electrode or membrane, one or both of the first silicon device layer 408 and second silicon device layer 410 may be doped to act as conductors, and in some cases are highly doped (e.g., having a doping concentration greater than $10^{15}$ dopants/$cm^3$ or greater).

The engineered substrate 402 may further include an oxide layer 414 on top of the second silicon device layer 410, which may represent the BOX layer of a silicon-on-insulator (SOI) wafer used to form the engineered substrate 402. The oxide layer 414 may function as a passivation layer in some embodiments and, as shown, may be patterned to be absent over the cavities 406. Contacts 424, and passivation layer 430 may be included on the engineered substrate 402. The passivation layer 430 may be patterned to allow access to one or more contacts 424, and may be formed of any suitable passivating material. In some embodiments, the passivation layer 430 is formed of silicon nitride $Si_3N_4$ and in some embodiments is formed by a stack of $SiO_2$ and $Si_3N_4$, although alternatives are possible.

The engineered substrate 402 and CMOS wafer 404 may be bonded together at bond points 416a and 416b. The bond points may represent eutectic bond points, for example formed by a eutectic bond of a layer on engineered substrate 402 with a layer on CMOS wafer 404, or may be any other suitable bond type described herein (e.g., a silicide bond or thermocompression bond). In some embodiments, the bond points 416a and 416b may be conductive, for example being formed of metal. The bond points 416a may function solely as bond points in some embodiments, and in some embodiments may form a seal ring, for example hermetically sealing the ultrasonic transducers of the device 400, and improving device reliability. In some embodiments, the bond points 416a may define a seal ring that also provides electrical connection between the engineered substrate and CMOS wafer. Similarly, the bond points 416b may serve a dual purpose in some embodiments, for example serving as bond points and also providing electrical connection between the ultrasonic transducers of the engineered substrate 402 and the IC of the CMOS wafer 404. In those embodiments in which the engineered substrate is not bonded with a CMOS wafer the bond points 416b may provide electrical connection to any electrical structures on a substrate to which the engineered substrate is bonded.

The CMOS wafer 404 includes a base layer a bulk silicon wafer) 418, an insulating layer 420 (e.g., $SiO_2$), and a metallization 422. The metallization 422 may be formed of aluminum, copper, or any other suitable metallization material, and may represent at least part of an integrated circuit formed in the CMOS wafer. For example, metallization 422 may serve as a routing layer, may be patterned to form one or more electrodes, or may be used for other functions. In practice, the CMOS wafer 404 may include multiple metallization layers and/or post-processed redistribution layers, but for simplicity, only a single metallization is illustrated.

The bond points 416b may provide electrical connection between the metallization 422 of CMOS wafer 404 and the first silicon device layer 408 of the engineered substrate. In this manner, the integrated circuitry of the CMOS wafer 404 may communicate with (e.g., send electrical signals to and/or receive electrical signals from) the ultrasonic transducer electrodes and/or membranes of the engineered substrate. In the illustrated embodiments, a separate bond point 416b is illustrated as providing electrical connection to each sealed cavity (and therefore for each ultrasonic transducer), although not all embodiments are limited in this manner. For example, in some embodiments, the number of electrical contacts provided may be less than the number of ultrasonic transducers.

Electrical contact to the ultrasonic transducer membranes represented by second silicon device layer 410 is provided in this non-limiting example by contacts 424, which may be formed of metal or any other suitable conductive contact material. In some embodiments, an electrical connection may be provided between the contacts 424 and the bond pad 426 on the CMOS wafer. For example, a wire bond 425 may be provided or a conductive material (e.g., metal) may be deposited over the upper surface of the device and patterned to form a conductive path from the contacts 424 to the bond pad 426. However, alternative manners of connecting the contacts 424 to the IC on the CMOS wafer 404 may be used. In some embodiments an embedded via (not shown in FIG. 4) may be provided from the first silicon device layer 408 to a bottom side of the second silicon device layer 410, thus obviating any need for the contacts 424 on the topside of the second silicon device layer 410. In such embodiments, suitable electrical isolation may be provided relative to any such via to avoid electrically shorting the first and second silicon device layers.

The device 400 also includes isolation structures (e.g., isolation trenches) 428 configured to electrically isolate groups of ultrasonic transducers (referred to herein as "ultrasonic transducer elements") or, as shown in FIG. 4, individual ultrasonic transducers. The isolation structures 428 may include trenches through the first silicon device layer 408 that are filled with an insulating material in some embodiments. Alternatively, the isolation structures 428 may be formed by suitable doping. Isolation structures 428 are optional.

Various features of the device 400 are now noted. For instance, it should be appreciated that the engineered substrate 402 and CMOS wafer 404 wafer may be monolithically integrated, thus providing for monolithic integration of ultrasonic transducers with CMOS ICs. In the illustrated embodiment, the ultrasonic transducers are positioned vertically (or stacked) relative to the CMOS IC, which may facilitate formation of a compact ultrasound device by reducing the chip area required to integrate the ultrasonic transducers and CMOS IC.

Additionally, the engineered substrate 402 includes only two silicon layers 408 and 410, with the cavities 406 being formed between them. The first silicon device layer 408 and second silicon device layer 410 may be thin, for example each being less than 50 microns in thickness, less than 30 microns in thickness, less than 20 microns in thickness, less than 10 microns in thickness, less than 5 microns in thickness, less than 3 microns in thickness, or approximately 2 microns in thickness, among other non-limiting examples. In some embodiments it is preferable for one of the two wafers (e.g., silicon layer 408 or silicon layer 410) of the engineered substrate to be sufficiently thick to minimize vibration, prevent vibration or shift the frequency of unwanted vibration to a range outside of the operating range of the device, thereby preventing interference. Through modeling of the geometries in the physical stack of the transducer integrated with the CMOS, thicknesses of all layers can be optimized for transducer center frequency and bandwidth, with minimal interfering vibration. This may include, but is not limited to, changing layer thicknesses and features in the transducer engineered substrate and changing the thickness of the CMOS wafer 418. These layer thicknesses are also chosen to provide uniformity across the area of the array, and therefore tighter frequency uniformity, using commercially available wafers.

Thus, while the engineered substrate may be thin, it may have a thickness of at least, for example, 4 microns in some embodiments, at least 5 microns in some embodiments, at least 7 microns in some embodiments, at least 10 microns in some embodiments, or other suitable thickness to prevent unwanted vibration. Such dimensions contribute to achieving a small device and may facilitate making electrical contact to the ultrasonic transducer membrane e.g., second silicon device layer 410) without the need for thru-silicon vias (TSVs). TSVs are typically complicated and costly to implement, and thus avoiding use of them may increase manufacturing yield and reduce device cost. Moreover, forming TSVs requires special fabrication tools not possessed by many commercial semiconductor foundries, and thus avoiding the need for such tools can improve the supply chain for forming the devices, making them more commercially practical than if TSVs were used.

The engineered substrate 402 as shown in FIG. 4 may be relatively thin, for example being less than 100 microns in total thickness, less than 50 microns in total thickness, less than 30 microns in total thickness, less than 20 microns in total thickness, less than 10 microns in total thickness, or any other suitable thickness. The significance of such thin dimensions includes the lack of structural integrity and the inability to perform various types of fabrication steps (e.g., wafer bonding, metallization, lithography and etch) with layers having such initially thin dimensions. Thus, it is noteworthy that such thin dimensions may be achieved in the device 400, via a process sequence.

Also, the silicon device layers 408 and 410 may be formed of single crystal silicon. The mechanical and electrical properties of single crystal silicon are stable and well understood, and thus the use of such materials in an ultrasonic transducer (e.g., as the membrane of a CMUT) may facilitate design and control of the ultrasonic transducer behavior.

In one embodiment, there is a gap between parts of the CMOS wafer 404 and the first silicon device layer 408 since the two are bonded at discrete bond points 416b rather than by a bond covering the entire surface of the CMOS wafer 404. The significance of this gap is that the first silicon device layer 408 may vibrate if it is sufficiently thin. Such vibration may be undesirable, for instance representing unwanted vibration in contrast to the desired vibration of the second silicon device layer 410. Accordingly, it is beneficial in at least some embodiments for the first silicon device layer 408 to be sufficiently thick to minimize vibration, avoid vibration or shift the frequency of any unwanted vibration outside of the operating frequency range of the device.

In alternative embodiments, it may be desirable for both the first and second silicon device layers 408 and 410 to vibrate. For instance, they may be constructed to exhibit different resonance frequencies, thus creating a multi-frequency device. The multiple resonance frequencies (which may be related as harmonics in some embodiments') may be used, for example, in different operating states of an ultrasonic transducer. For example, the first silicon device layer 408 may be configured to resonate at half the center frequency of the second silicon device layer 410.

In still another embodiment, the strength of the bond between silicon device layer 410 and silicon oxide layer 412 allows for cavities 406 formed within silicon oxide layer 412 to have a larger diameter than would be possible with a weaker bond between layers 410 and 412. The diameter of a cavity is indicated as "w" in FIG. 4. The bond strength is provided at least in part by using a fabrication process in which the engineered substrate 402 is formed by bonding (e.g., at temperature less than about 400° C.) of two wafers, one containing silicon device layer 408 and the other containing silicon device layer 410, followed by a high temperature anneal (e.g., about 1000° C.). Ultrasonic transducers implemented using wide cavities may generate ultrasonic signals having more power at a particular frequency than ultrasonic signals generated at the same particular frequency by ultrasonic transducers implemented using cavities have a smaller diameter. In turn, higher power ultrasonic signals penetrate deeper into a subject being imaged thereby enabling high-resolution imaging of a subject at greater depths than possible with ultrasonic transducers having smaller cavities. For example, conventional ultrasound probes may use high frequency ultrasound signals (e.g., signals having frequencies in the 7-12 MHz range) to generate high-resolution images, but only at shallow depths due to the rapid attenuation of high-frequency ultrasound signals in the body of a subject being imaged. However, increasing the power of the ultrasonic signals emitted by an ultrasound probe (e.g., as enabled through the use of cavities having a larger diameter as made possible by the strength of the bond between layers 410 and 412) allows the ultrasonic signals to penetrate the subject deeper resulting in high-resolution images of the subject at greater depths than previously possible with conventional ultrasound probes.

Additionally, an ultrasonic transducer formed using a larger diameter cavity may generate lower frequency ultrasound signals than an ultrasonic transducer having a cavity with a smaller diameter. This extends the range of frequencies across which the ultrasonic transducer may operate. An additional technique mat be to selectively etch and thin portions of the transducer top membrane 410. This introduces spring softening in the transducer membrane, thereby lowering the center frequency. This may be done on all, some or none of the transducers in the array in any combination of patterns.

Forms of Universal Ultrasound Device

A universal ultrasound device may be implemented in any of a variety of physical configurations including, for example, as a part of a pill to be swallowed by a subject, as part of a handheld device including a screen to display obtained images, as part of a patch configured to be affixed to the subject, or as part of a hand-held probe.

In some embodiments, a universal ultrasound probe may be embodied in a pill to be swallowed by a subject. As the pill travels through the subject, the ultrasound probe within the pill may image the subject and wirelessly transmit obtained data to one or more external devices for processing the data received from the pill and generating one or more images of the subject. For example, as shown in FIG. 5A, pill 502 comprising an ultrasound probe may be configured to communicate wirelessly (e.g., via wireless link 501) with external device 500, which may be a desktop, a laptop, a handheld computing device, and/or any other device external to pill 502 and configured to process data received from pill 502. A person may swallow pill 502 and, as pill 502 travels through the person's digestive system, pill 502 may image the person from within and transmit data obtained by the ultrasound probe within the pill to external device 500 for further processing.

Figure 5B:
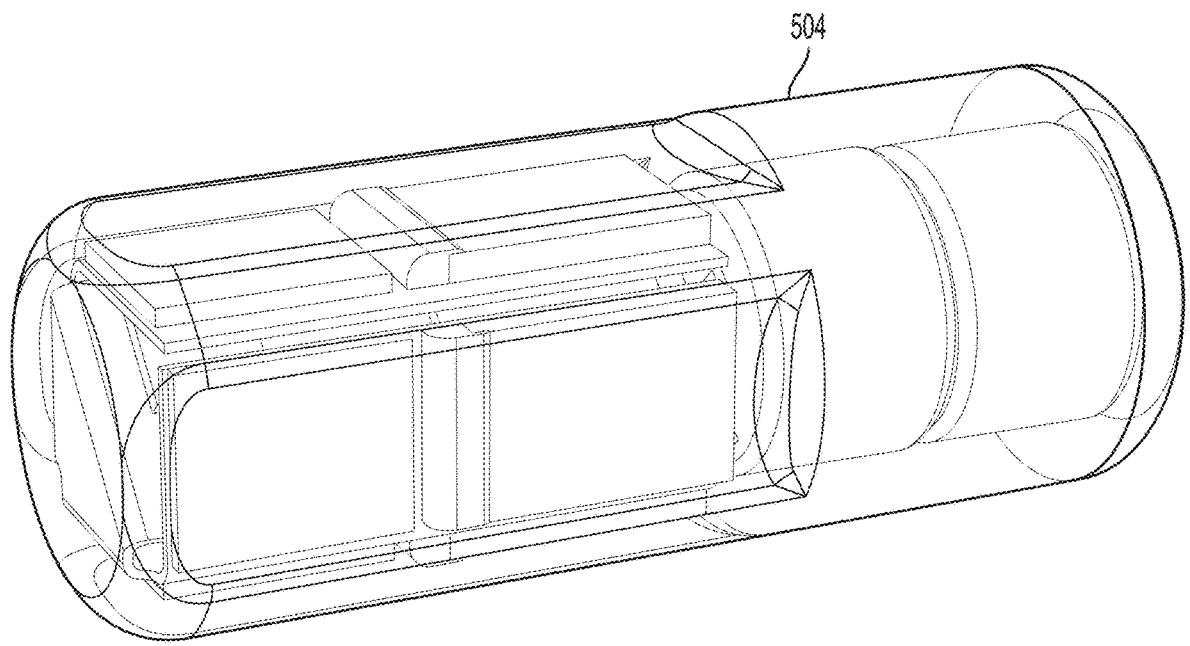
Figure 5C:
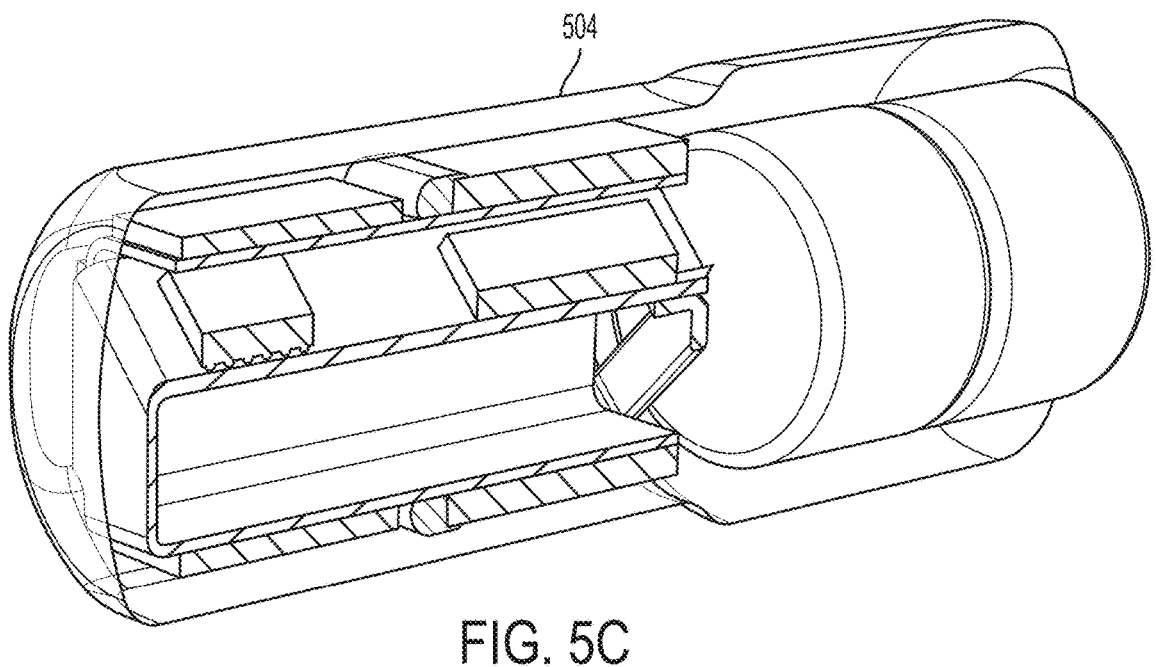
Figure 5D:
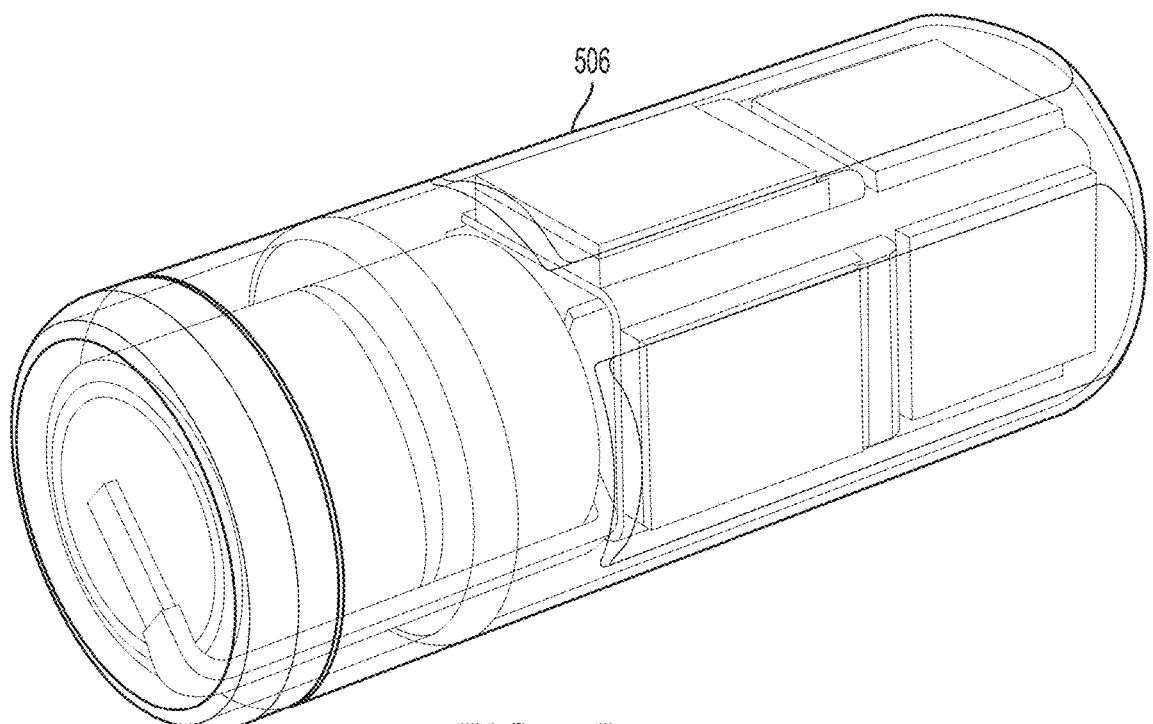
Figure 5E:
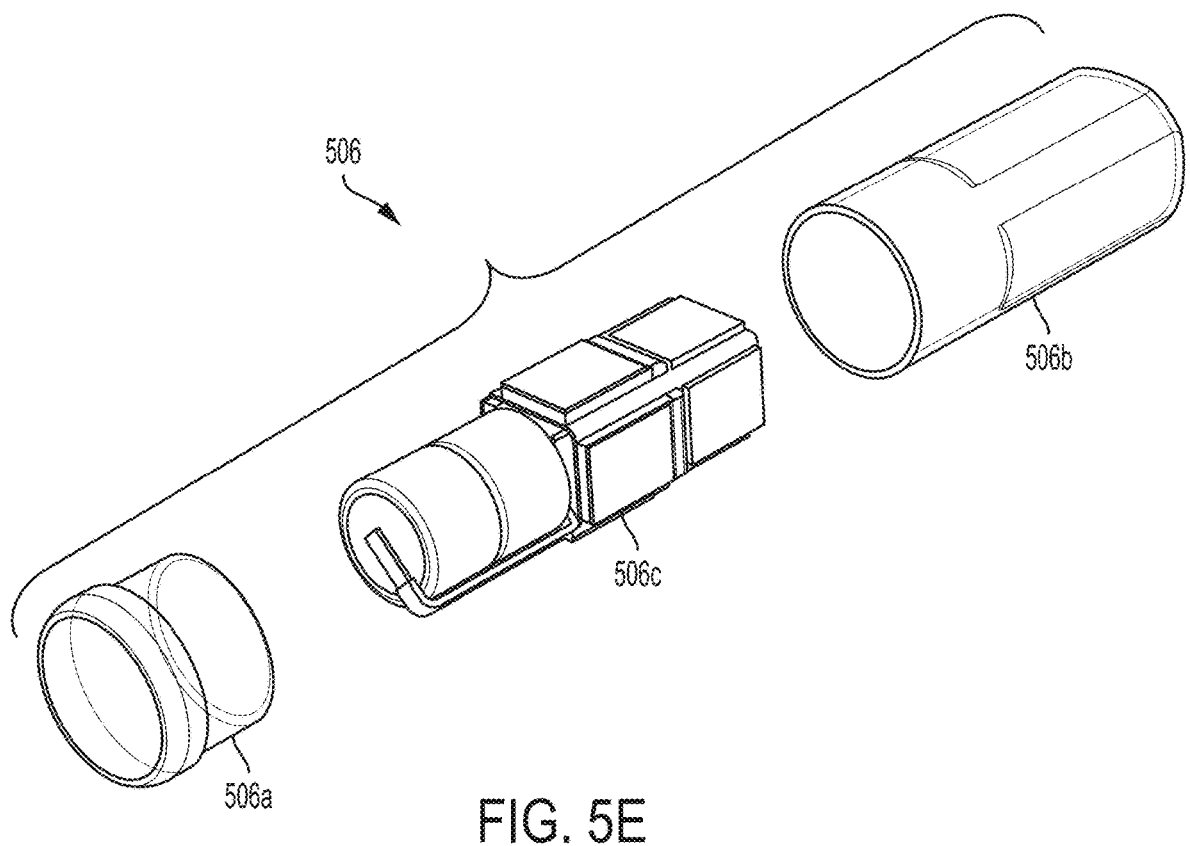
Figure 6A:
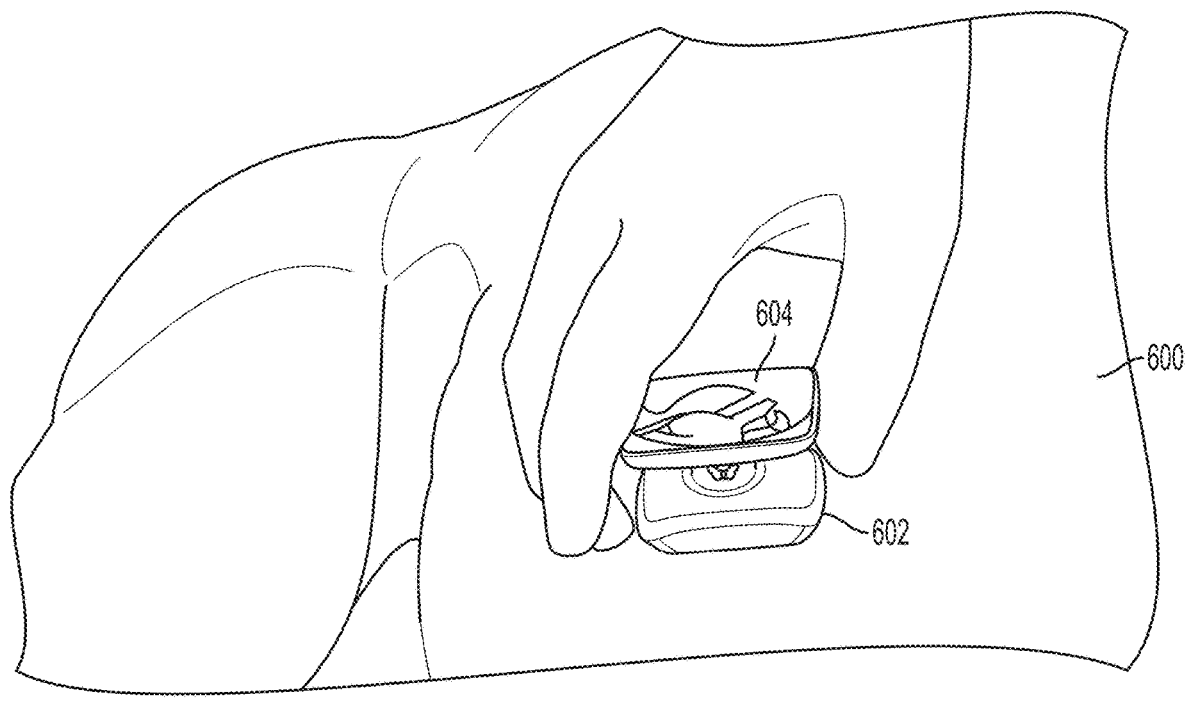
FIGS. 6A-6B illustrate a handheld device comprising an ultrasound probe and a display, in accordance with some embodiments of the technology described herein.
Figure 6B:
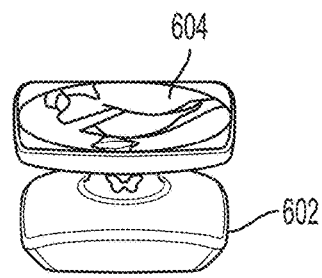

In some embodiments, a pill comprising an ultrasound probe may be implemented by potting the ultrasound probe within an outer case, as illustrated by an isometric view of pill 504 shown in FIG. 5B. FIG. 5C is a section view of pill 504 shown in FIG. 5B exposing views of the electronic assembly and batteries. In some embodiments, a pill comprising an ultrasound probe may be implemented by encasing the ultrasound probe within an outer housing, as illustrated by an isometric view of pill 506 shown in FIG. 5D. FIG. 5E is an exploded view of pill 506 shown in FIG. 5D showing outer housing portions 510a and 510b used to encase electronic assembly 510c.

Figure 5F:
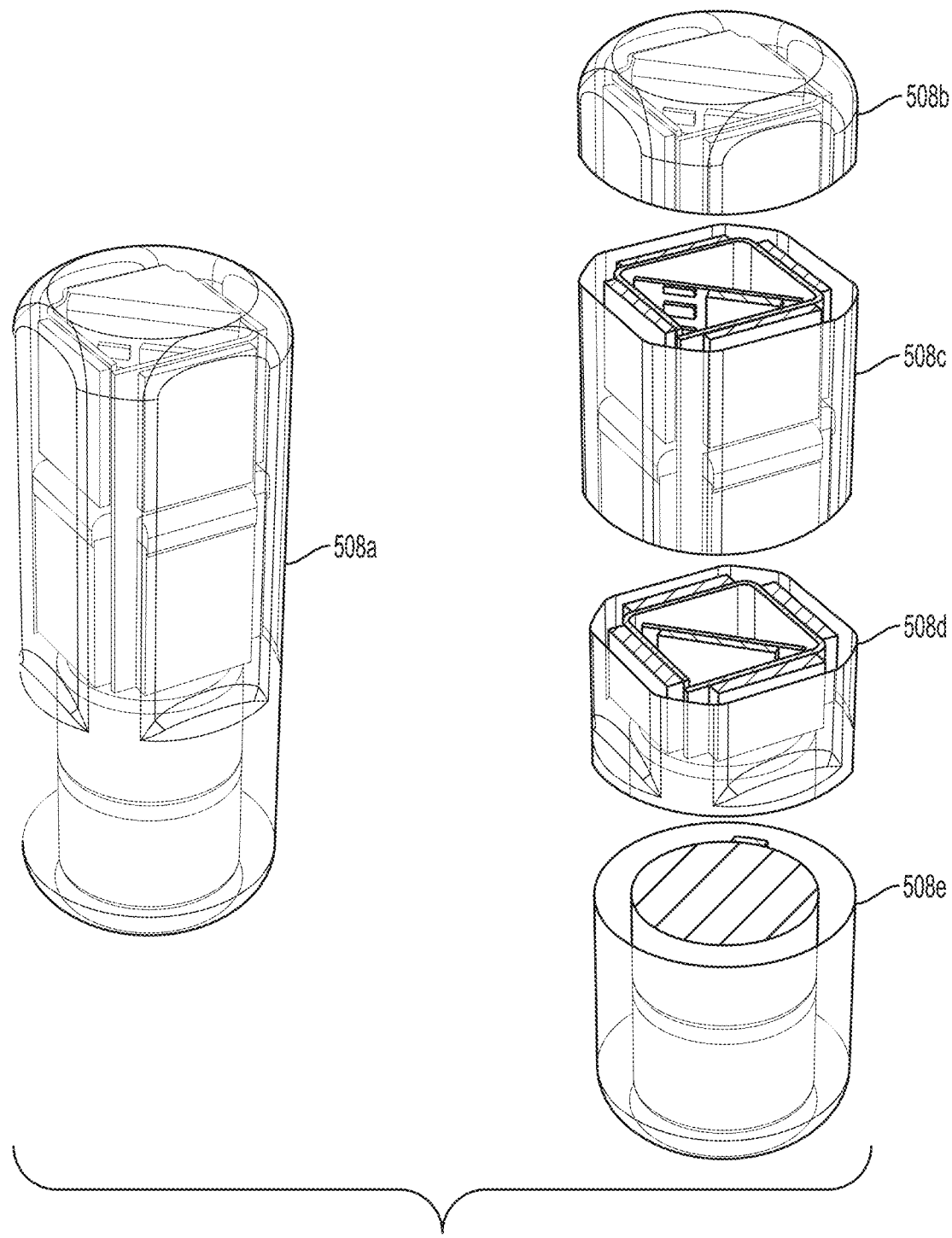
Figure 5G:
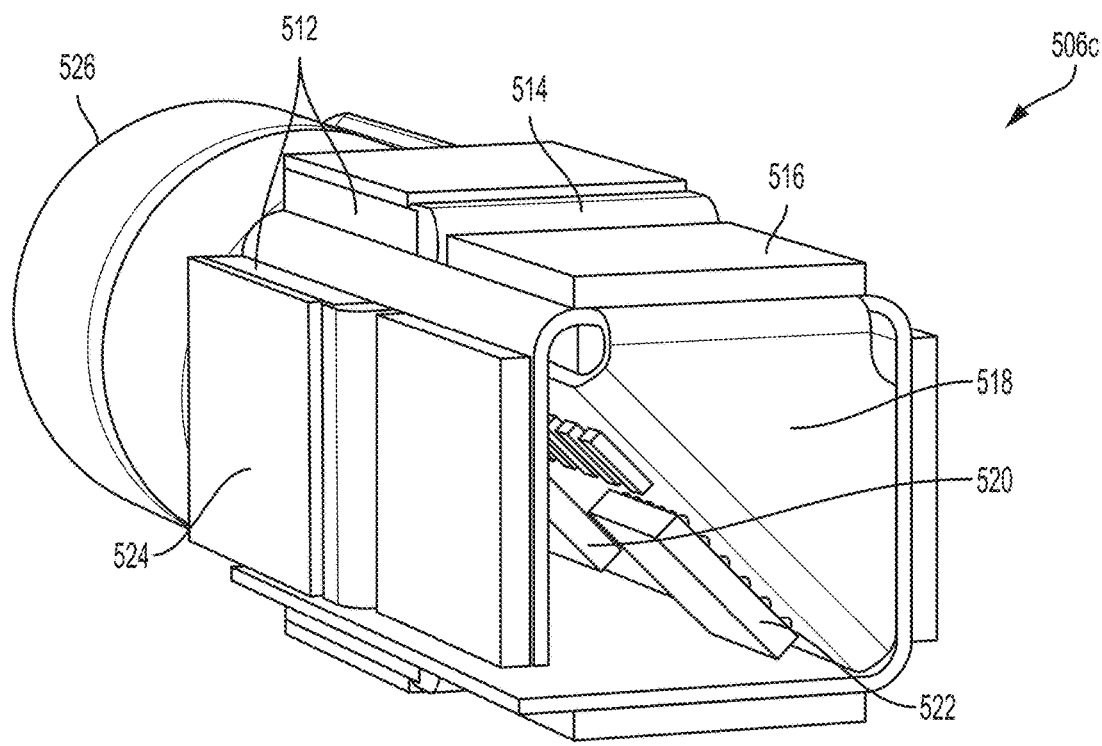
Figure 5H:
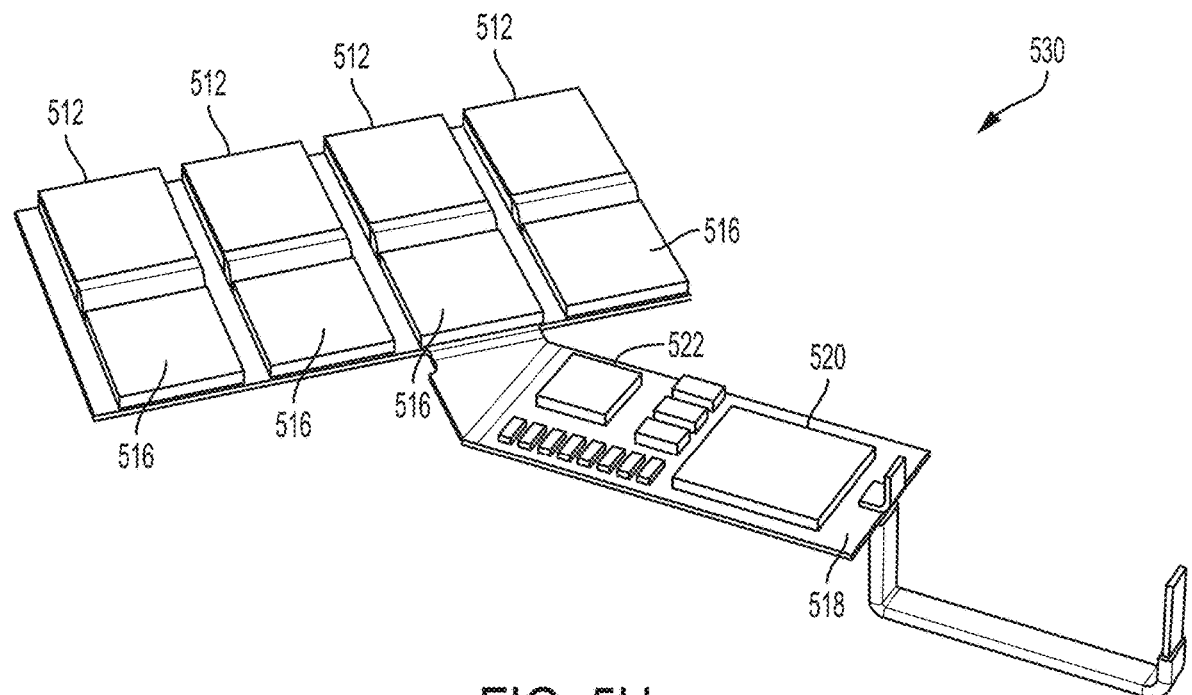

In some embodiments, the ultrasound probe implemented as part of a pill may comprise one or multiple ultrasonic transducer (e.g., CMUT) arrays, one or more image reconstruction chips, an FPGA, communications circuitry, and one or more batteries. For example, as shown in FIG. 5F, pill 508a may include multiple ultrasonic transducer arrays shown in sections 508b and 508c, multiple image reconstruction chips as shown in sections 508c and 508d, a WiFi chip as shown in section 508d, and batteries as shown in sections 508d and 508e.

FIGS. 5G and 5H further illustrate the physical configuration of electronics module 506c shown in FIG. 5E. As shown in FIGS. 5G and 5H, electronics module 506c includes four CMUT arrays 512 (though more or fewer CMUT arrays may be used in other embodiments), bond wire encapsulant 514, four image reconstruction chips 516 (though more or fewer image reconstruction chips may be used in other embodiments), flex circuit 518, WiFi chip 520, FPGA 522, and batteries 522. Each of the batteries may be of size 13 PR48. Each of the batteries may be a 300 mAh 1.4V battery. Other batteries may be used, as aspects of the technology described herein are not limited in this respect.

In some embodiments, the ultrasonic transducers of an ultrasound probe in a pill are physically arranged such that the field of view of the probe within the pill is equal to or as close to 360 degrees as possible. For example, as shown in FIGS. 5G and 5H, each of the four CMUT arrays may a field of view of approximately 60 degrees (30 degrees on each side of a vector normal to the surface of the CMUT array) or a field of view in a range of 40-80 degrees such that the pill consequently has a field of view of approximately 240 degrees or a field of view in a range of 160-320 degrees.

In some embodiments, a universal ultrasound probe may be embodied in a handheld device 602 illustrated in FIGS. 6A and 6B. Handheld device 602 may be held against (or near) a subject 600 and used to image the subject. Handheld device 602 may comprise an ultrasound probe (e.g., a universal ultrasound probe) and display 604, which in some embodiments, may be a touchscreen. Display 604 may be configured to display images of the subject generated within handheld device 602 using ultrasound data gathered by the ultrasound probe within device 602.

In some embodiments, handheld device 602 may be used in a manner analogous to a stethoscope. A medical professional may place handheld device 602 at various positions along a patient's body. The ultrasound probe within handheld device 602 may image the patient. The data obtained by the ultrasound probe may be processed and used to generate image(s) of the patient, which image(s) may be displayed to the medical professional via display 604. As such, a medical professional could carry hand-held device (e.g., around their neck or in their pocket) rather than carrying around multiple conventional probes, which is burdensome and impractical.

Figure 7A:
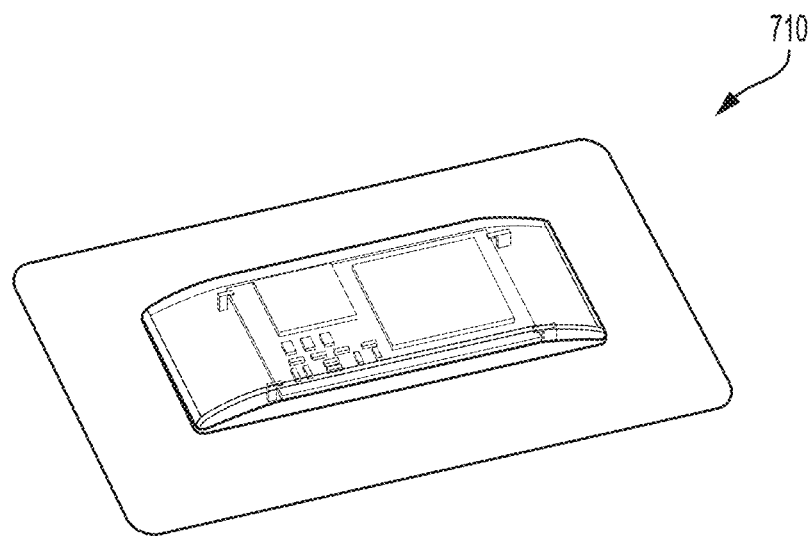
FIGS. 7A-7B illustrate a patch comprising an ultrasound probe, in accordance with some embodiments of the technology described herein.
Figure 7B:
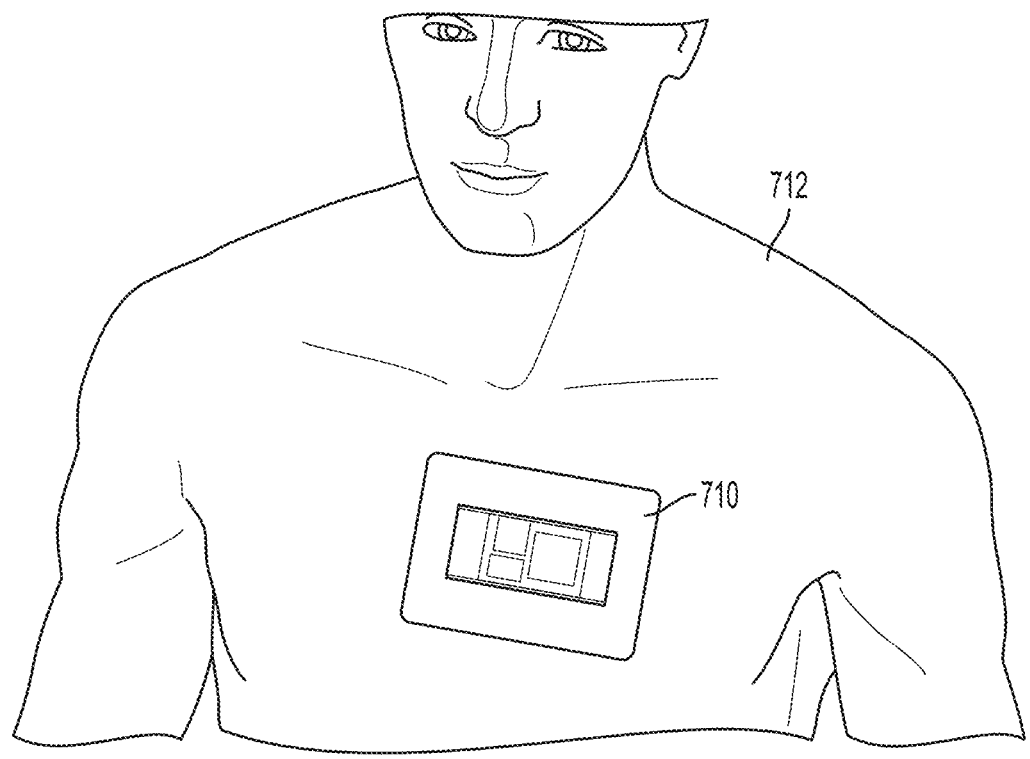

In some embodiments, a universal ultrasound probe may be embodied in a patch that may be coupled to a patient. For example, FIGS. 7A and 7B illustrate a patch 710 coupled to patient 712. The patch 710 may be configured to transmit, wirelessly for example, data collected by the patch 710 to one or more external devices (not shown) for further processing. For purposes of illustration, a top housing of the patch 710 is depicted in a transparent manner to depict exemplary locations of various internal components of the patch.

Figure 7C:
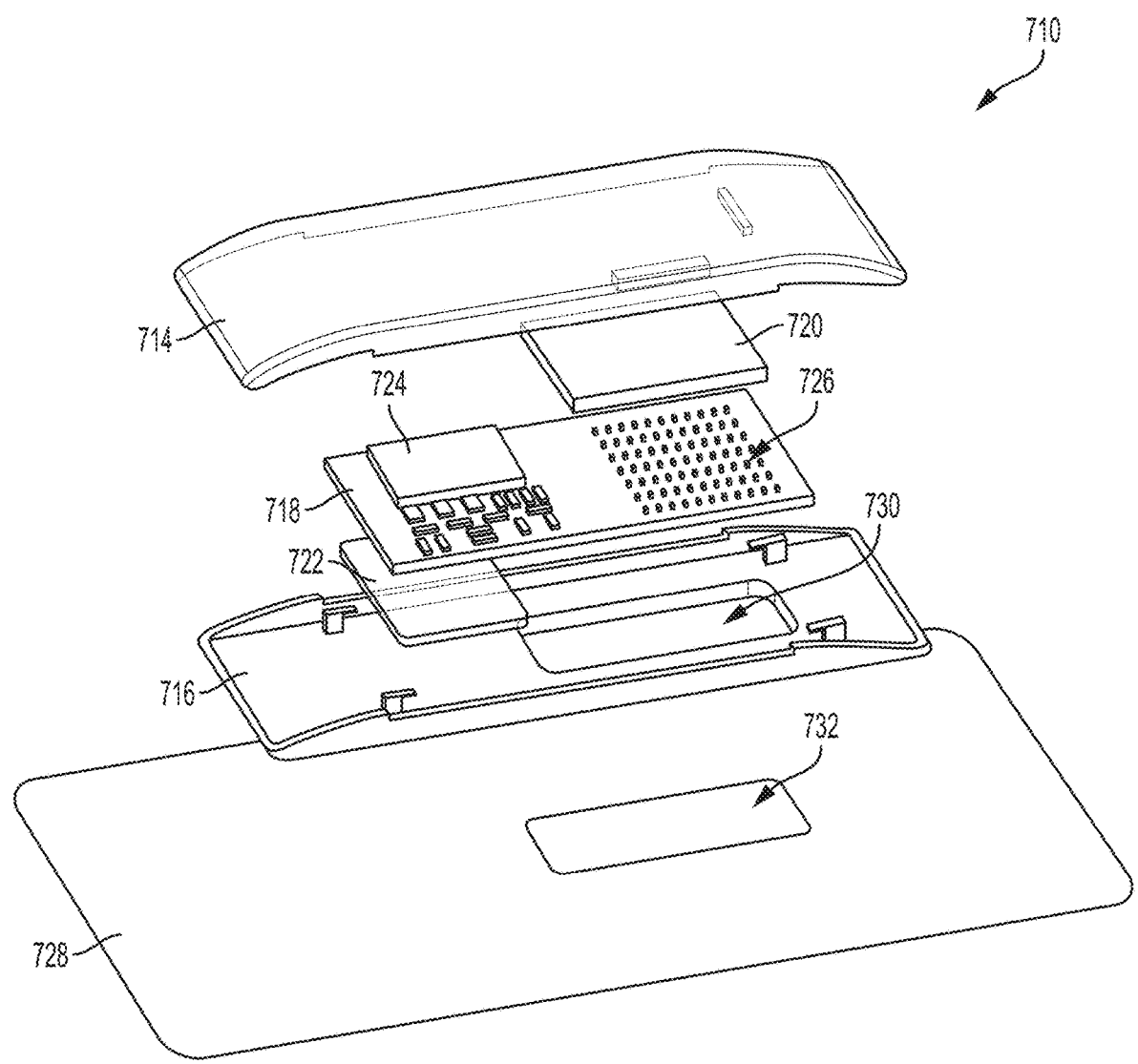
Figure 7D:
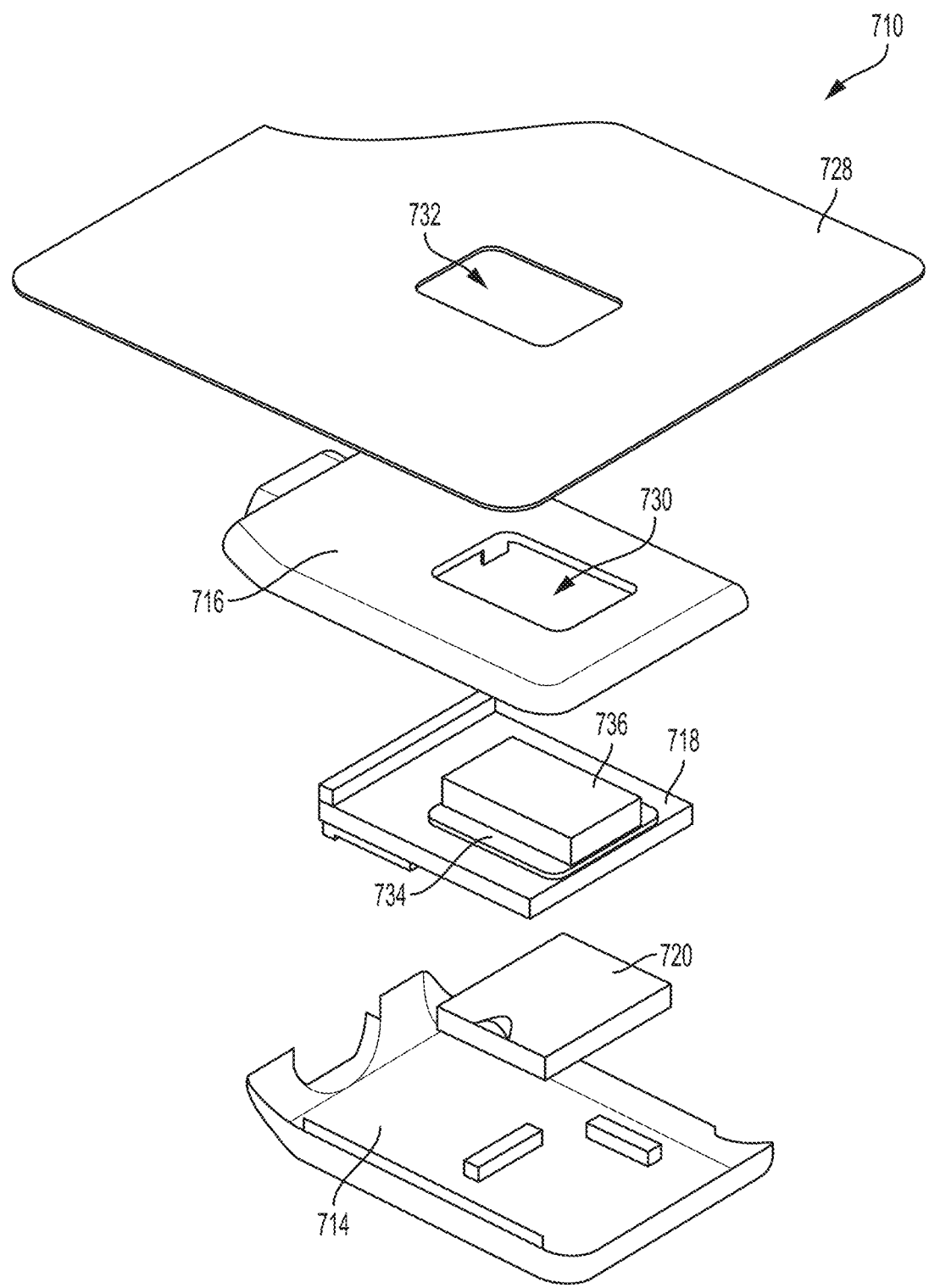

FIGS. 7C and 7D show exploded views of patch 710. As particularly illustrated in FIG. 7C, patch 710 includes upper housing 714, lower housing 716, and circuit board 718. Circuit board 718 may be configured to support various components, such as for example heat sink 720, battery 722 and communications circuitry 724. In one embodiment, communication circuitry 724 includes one or more short- or long-range communication platform. Exemplary short-range communication platforms include, Bluetooth (BT), Bluetooth Low Energy (BLE), Near-Field Communication (NFC). Long-range communication platforms include, WiFi and Cellular. While not shown, the communication platform may include front-end radio, antenna and other processing circuitry configured to communicate radio signal to and auxiliary device (not shown). The radio signal may include ultrasound imaging information obtained by patch 710.

In an exemplary embodiment, communication circuitry transmits periodic beacon signals according to IEEE 802.11 and other prevailing standards. The beacon signal may include a BLE advertisement. Upon receipt of the beacon signal or the BLE advertisement, an auxiliary device (not shown) may respond to patch 710. That is, the response to the beacon signal may initiate a communication handshake between patch 710 and the auxiliary device.

The auxiliary device may include laptop, desktop, smartphone or any other device configured for wireless communication. The auxiliary device may act as a gateway to cloud or internet communication. In an exemplary embodiment, the auxiliary device may include the patient's own smart device (e.g., smartphone) which communicatively couples to patch 710 and periodically receives ultrasound information from patch 710. The auxiliary device may then communicate the received ultrasound information to external sources.

Circuit board 718 may comprise one or more processing circuitry, including one or more controllers to direct communication through communication circuitry 724. For example, circuit board 718 may engage communication circuitry periodically or on as-needed basis to communicate information with one or more auxiliary devices. Ultrasound information may include signals and information defining an ultrasound image captured by patch 710. Ultrasound information may also include control parameters communicated from the auxiliary device to patch 710. The control parameters may dictate the scope of the ultrasound image to be obtained by patch 710.

In one embodiment, the auxiliary device may store ultrasound information received from patch 710. In another embodiment, the auxiliary device may relay ultrasound information received from patch 710 to another station. For example, the auxiliary device may use Wi-Fi to communicate the ultrasound information received from patch 710 to a cloud-based server. The cloud-based server may be a hospital server or a server accessible to the physician directing ultrasound imaging. In another exemplary embodiment, patch 710 may send sufficient ultrasound information to the auxiliary device such that the auxiliary device may construct an ultrasound image therefrom. In this manner, communication bandwidth and power consumption may be minimized at patch 710.

In still another embodiment, the auxiliary device may engage patch 710 through radio communication (i.e., through communication circuitry 724) to actively direct operation of patch 710. For example, the auxiliary device may direct patch 710 to produce ultrasound images of the patient at periodic intervals. The auxiliary device may direct the depth of the ultrasound images taken by patch 710. In still another example, the auxiliary device may control the manner of operation of the patch so as to preserve power consumption at battery 722. Upon receipt of ultrasound information from patch 710, the auxiliary device may operate to cease imaging, increase imaging rate or communicate an alarm to the patient or to a third party (e.g., physician or emergency personnel).

It should be noted that the communication platform described in relation with FIG. 7 may also be implemented in other form-factors disclosed herein. For example, the communication platform (including control circuitry and any interface) may be implemented in the ultrasound pill as illustrated in FIGS. 5A-5H, the handheld device as illustrated in FIGS. 6A-6B or the handheld probe as illustrated in FIG. 8.

As shown in FIG. 7C, a plurality of through vias 726 (e.g., copper) may be used for a (hernial connection between heat sink 720 and one or more image reconstruction chips (e.g., CMOS) (not shown in FIG. 7C). As further depicted in FIG. 7C, patch 710 may also include dressing 728 that provides an adhesive surface for both the patch housing as well as to the skin of a patient. One non-limiting example of such a dressing 728 is Tegaderm™, a transparent medical dressing available from 3M Corporation. Lower housing 716 includes a generally rectangular shaped opening 730 that aligns with another opening 732 in dressing 728.

Referring to FIG. 7D, another "bottom up" exploded view of the patch 710 illustrates the location of ultrasonic transducers and integrated CMOS chip (generally indicated by 734) on circuit board 718. An acoustic lens 736 mounted over the transducers/CMOS 734 is configured to protrude through openings 730, 732 to make contact with the skin of a patient. Although the embodiment of FIGS. 7A-7D depict an adhesive dressing 728 as a means of affixing patch 710 to patient 712, it will be appreciated that other fastening arrangements are also contemplated. For example, a strap (not shown) may be used in lieu of (or in addition to) dressing 728 in order to secure the patch 710 at a suitable imaging location.

Figure 8:
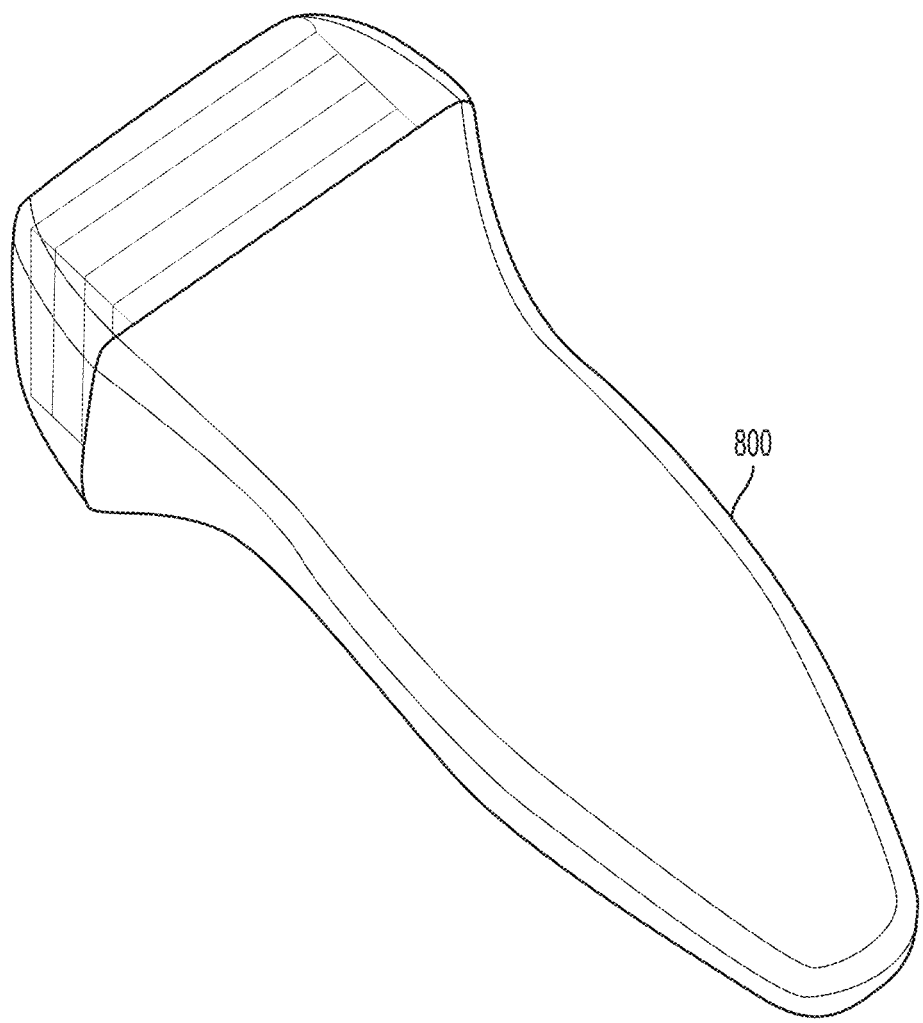
FIG. 8 is a diagram illustrating a handheld probe comprising an ultrasound probe, in accordance with some embodiments of the technology described herein.

In some embodiments, a universal ultrasound probe may be embodied in hand-held probe 800 shown in FIG. 8. Hand-held probe 800 may be configured to transmit data collected by the probe 800 wirelessly to one or more external host devices (not shown in FIG. 8) for further processing. In other embodiments, hand-held probe 800 may be configured transmit data collected by the probe 800 to one or more external devices using one or more wired connections, as aspects of the technology described herein are not limited in this respect.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The following non-limiting exemplary embodiments are provided to illustrate inventive aspects of the disclosure.

Example 1 is directed to an ultrasound device, comprising: an ultrasound probe, including a semiconductor die, and a plurality of ultrasonic transducers integrated on the semiconductor die, the plurality of ultrasonic transducers configured to operate in a first mode associated with a first frequency range and a second mode associated with a second frequency range, wherein the first frequency range is at least partially non-overlapping with the second frequency range; and control circuitry configured to: control the plurality of ultrasonic transducers to generate and/or detect ultrasound signals having frequencies in the first frequency range, in response to receiving an indication to operate the ultrasound probe in the first mode; and control the plurality of ultrasonic transducers to generate and/or detect ultrasound signals having frequencies in the second frequency range, in response to receiving an indication to operate the ultrasound probe in the second mode.

Example 2 is directed to the ultrasound device of example 1, wherein a width of the first frequency range is at least 1 MHz and a width of the second frequency range is at least 1 MHz.

Example 3 is directed to the ultrasound device of example 1, wherein a difference between a first center frequency in the first frequency range and a second center frequency in the second frequency range is at least 1 MHz.

Example 4 is directed to the ultrasound device of example 3, wherein the difference is at least 2 MHz.

Example 5 is directed to the ultrasound device of example 4, wherein the difference is between about 6 MHz and about 9 MHz.

Example 6 is directed to the ultrasound device of example 1, wherein the first frequency range is contained entirely within a range of 1-5 MHz.

Example 7 is directed to the ultrasound device of example 6, herein the first frequency range is contained entirely within a range of 2-4 MHz.

Example 8 is directed to the ultrasound device of example 1, wherein the second frequency range is contained entirely within a range of 5-9 MHz.

Example 9 is directed to the ultrasound device of example 8, wherein the second frequency range is contained entirely within a range of 6-8 MHz.

Example 10 is directed to the ultrasound device of example 1, the plurality of ultrasonic transducers is further configured to operate in a third mode associated with a third frequency range that is at least partially non-overlapping with the first frequency range and the second frequency range, and wherein the control circuitry is further configured to: control the plurality of ultrasonic transducers to generate and/or detect ultrasound signals having frequencies in the third frequency range, in response to receiving an indication to operate the ultrasound probe in the third mode.

Example 11 is directed to the ultrasound device of example 10, wherein the first frequency range is contained entirely within a range of 1-3 MHz, the second frequency range is contained entirely within a range of 3-7 MHz, and the third frequency range is contained entirely within a range of 7-15 MHz.

Example 12 is directed to the ultrasound device of example 1, wherein: when the plurality of ultrasonic transducers are controlled to detect ultrasound signals having frequencies in the first frequency range, ultrasound signals detected by the plurality of ultrasonic transducers are used to form an image of a subject up to a first depth within the subject; and when the plurality of ultrasonic transducers are controlled to detect ultrasound signals having frequencies in the second frequency range, ultrasound signals detected by the plurality of ultrasonic transducers are used to form an image of a subject up to a second depth within the subject, wherein the second depth is smaller than the first depth.

Example 13 is directed to the ultrasound device of example 12, wherein the first depth is contained within a range of up to 8-25 cm from a surface of the subject.

Example 14 is directed to the ultrasound device of example 13, wherein the first depth is contained within a range of up to 15-20 cm from the surface of the subject.

Example 15 is directed to the ultrasound device of example 12, wherein the second depth is contained within a range of up to 3-7 cm from a surface of the subject.

Example 16 is directed to the ultrasound device of example 1, wherein the plurality of ultrasound transducers are capacitive ultrasonic transducers, and wherein the control circuitry is configured to control the plurality of ultrasonic transducers to generate and/or detect ultrasound signals having frequencies in the second frequency range at least in part by causing the plurality of ultrasonic transducers to operate in a collapsed mode, in which at least one portion of a membrane of the plurality of ultrasonic transducers is mechanically fixed and at least one portion of the membrane is free to vibrate based on a changing voltage differential between an electrode and the membrane.

Example 17 is directed to the ultrasound device of example 1, wherein the control circuitry is configured to: cause a first voltage to be applied to the plurality of ultrasonic transducers in response to the indication to operate the ultrasound probe in the first frequency range; and cause a second voltage to be applied to the plurality of ultrasonic transducers in response to the indication to operate the ultrasound probe in the second frequency range, wherein the second voltage is higher than the first voltage.

Example 18 is directed to the ultrasound device of example 17, wherein the second voltage is greater than a collapse voltage for the plurality of ultrasonic transducers, the collapse voltage comprising a voltage which causes a membrane of an ultrasonic transducers to make contact to a bottom of a cavity of the ultrasonic transducer.

Example 19 is directed to the ultrasound device of example 18, wherein the collapse voltage is at least 30 volts.

Example 20 is directed to the ultrasound device of example 1, wherein the plurality of ultrasonic transducers includes multiple ultrasonic transducers at least one of which is configured to generate ultrasound signals in the first frequency range and in the second frequency range.

Example 21 is directed to the ultrasound device of example 1, wherein the plurality of ultrasonic transducers includes a plurality of CMOS ultrasonic transducers.

Example 22 is directed to the ultrasound device of example 21, wherein the plurality of CMOS ultrasonic transducers includes a first CMOS ultrasonic transducer including a cavity formed in a CMOS wafer, with a membrane overlying and sealing the cavity.

Example 23 is directed to the ultrasound device of example 1, wherein the plurality of ultrasonic transducers includes a plurality of micromachined ultrasonic transducers.

Example 24 is directed to the ultrasound device of example 23, wherein the plurality of micromachined ultrasonic transducers includes a plurality of capacitive micromachined ultrasonic transducers.

Example 25 is directed to the ultrasound device of example 23, wherein the plurality of micromachined ultrasonic transducers includes a plurality of piezoelectric ultrasonic transducers.

Example 26 is directed to the ultrasound device of example 1, wherein the ultrasound probe further comprises a handheld device.

Example 27 is directed to the ultrasound device of example 26, wherein the handheld device further comprises a display.

Example 28 is directed to the ultrasound device of example 26, wherein the handheld device further comprises a touchscreen.

Example 29 is directed to the ultrasound device of example 1, wherein the ultrasound probe comprises a patch configured to be affixed to a subject.

Example 30 is directed to a skin-mountable ultrasound patch, comprising: a monolithic ultrasound chip including a semiconductor die, and a plurality of ultrasonic transducers integrated on the semiconductor die, at least one of the plurality of ultrasonic transducers configured to operate in a first mode associated with a first frequency range and a second mode associated with a second frequency range, wherein the first frequency range is at least partially non-overlapping with the second frequency range; and a dressing configured to receive and retain the ultrasound chip, the dressing further configured to couple to a patient's body.

Example 31 is directed to the ultrasound patch of example 30, wherein the monolithic ultrasound chip further comprises a control circuitry configured to control the plurality of ultrasonic transducers to generate and/or detect ultrasound signals having frequencies in the first frequency range, in response to receiving an indication to operate the ultrasound probe in the first mode; and to control the plurality of ultrasonic transducers to generate and/or detect ultrasound signals having frequencies in the second frequency range, in response to receiving an indication to operate the ultrasound probe in the second mode.

Example 32 is directed to the ultrasound patch of example 31, wherein the control circuitry defines a CMOS circuitry.

Example 33 is directed to the ultrasound patch of example 30, wherein the dressing further comprises an adhesive layer to couple the patch to the patient's body.

Example 34 is directed to the ultrasound patch of example 30, further comprising a housing to receive the monolithic ultrasound chip, the housing having an upper portion and a lower portion, wherein the lower housing portion further comprises an aperture to expose the ultrasonic transducers to the subject's body.

Example 35 is directed to the ultrasound patch of example 30, further comprising a, communication platform to communicate ultrasound signals to and from the ultrasound chip.

Example 36 is directed to the ultrasound patch of example 30, further comprising a circuit board to receive the ultrasound chip.

Example 37 is directed to the ultrasound patch of example 30, further comprising a communication platform to communicate with an external communication device.

Example 38 is directed to the ultrasound patch of example 37, wherein the communication platform is selected from the group consisting of Near-Field Communication (NFC), Bluetooth (BT), Bluetooth Low Energy (BLE) and WiFi.

Example 39 is directed to a wearable ultrasound device, comprising: a ultrasound chip including an array of ultrasonic transducers, each ultrasonic transducer defining a capacitive micro-machined ultrasonic transducer (CMUT) operable to transceive signals; and a dressing configured to receive and retain the ultrasound chip, the dressing, further configured to couple to a subject body; wherein the array of ultrasonic transducers further comprises a first plurality of CMUTS configured to operate in a collapse mode and a second plurality of CMUTS configured to operation in a non-collapse mode.

Example 40 is directed to the wearable ultrasound device of example 39, wherein the ultrasound chip further comprises a control circuitry configured to control the plurality of ultrasonic transducers to generate and/or detect ultrasound signals having frequencies in the first frequency range, in response to receiving an indication to operate the ultrasound probe in the first mode; and to control the plurality of ultrasonic transducers to generate and/or detect ultrasound signals having frequencies in the second frequency range, in response to receiving an indication to operate the ultrasound probe in the second mode.

Example 41 is directed to the wearable ultrasound device of example 40, wherein the ultrasound chip defines a solid-state device.

Example 42 is directed to the wearable ultrasound device of example 39, wherein the ultrasonic transducer is configured to generate a first frequency band when operated at collapse mode and to generate a second frequency band when operated at non-collapse mode.

Example 43 is directed to the wearable ultrasound device of example 39, wherein the ultrasound chip is configured to switch between collapse and non-collapse modes of operation.

Example 44 is directed to the wearable ultrasound device of example 39, further comprising a communication platform to communicate with an external communication device.

Example 45 is directed to the wearable ultrasound device of example 44, wherein the communication platform is selected from the group consisting of Near-Field Communication (NFC), Bluetooth (BT), Bluetooth Low Energy (BLE) and WiFi.

Example 46 is directed to the wearable ultra-sound device of example 45, wherein the communication platform receives imaging instructions from an auxiliary device and transmits one or more ultrasound images to the auxiliary device in response to the received instructions.

Example 47 is directed to the wearable ultrasound device of example 39, wherein the dressing further comprises an opening to accommodate an optical lens adjacent the array of ultrasonic transducers.

The invention claimed is:
1. A universal ultrasound device, comprising:
a semiconductor die having an array of capacitive micromachined ultrasonic transducers (CMUTs);
a waveform generator on the semiconductor die and in communication with one or more of the CMUTs in the array, the waveform generator configured to produce a plurality of waveforms to be communicated through the one or more CMUTs; and
a controller coupled to the array of CMUTs and configured to:

in response to receiving an indication to operate in a first mode of operation having an associated first frequency range of operation,
    select, using information specifying, for the first mode of operation, a first azimuth aperture value or a first elevation aperture value, a first set of the CMUTs of the array making up a first active aperture occupying a first physical area of the semiconductor die; and
    control the first set of the CMUTs to generate and detect ultrasound signals having frequencies in the first frequency range; and
in response to receiving an indication to operate in a second mode of operation having an associated second frequency range of operation different than the first frequency range of operation,
    select, using information specifying, for the second mode of operation, a second azimuth aperture value different from the first azimuth aperture value or a second elevation aperture value different from the first elevation aperture value, a second set of the CMUTs of the array making up a second active aperture different than the first active aperture occupying a second physical area of the semiconductor die; and
    control the second set of the CMUTs to generate and detect ultrasound signals having frequencies in the second frequency range;
    wherein: (a) both the first and second modes of operation comprise collapse modes of operation; or (b) both the first and second modes of operation comprise non-collapsed modes of operation.

2. The universal ultrasound device of claim 1, wherein the first frequency range and the second frequency range overlap.

3. The universal ultrasound device of claim 1, wherein the first frequency range and the second frequency range do not overlap.

4. The universal ultrasound device of claim 1, wherein the first frequency range is in a range of about 1-5 MHz, with a center frequency of about 3 MHz.

5. The universal ultrasound device of claim 1, wherein the first frequency range is powered to penetrate an approximate depth of about 10-25 cm within a subject.

6. The universal ultrasound device of claim 1, wherein the second frequency range is in a range of about 5-12 MHz, with a center frequency of about 8 MHz.

7. The universal ultrasound device of claim 1, wherein the second frequency range is powered to penetrate an approximate depth of about 1-10 cm within a subject.

8. The universal ultrasound device of claim 1, wherein the controller is further configured to select, for a third mode of operation having an associated third frequency range of operation different than the first and second frequency ranges of operation, a third set of the CMUTs making up a third active aperture different than the first and second active apertures and occupying a third physical area of the semiconductor die.

9. The universal ultrasound device of claim 8, wherein the first frequency range is in a range of about 1-3 MHz, the second frequency range is in a range of about 3-7 MHz and the third frequency range is in a range of about 7-12 MHz.

10. The universal ultrasound device of claim 8, wherein the first frequency range is about 1-5 MHz, the second frequency range is about 3-7 MHz and the third frequency range is about 5-10 MHz.

11. The universal ultrasound device of claim 1, wherein the first frequency range and the second frequency range are associated with different elevational focal regions.

12. The universal ultrasound device of claim 1, wherein the controller is configured to select one of the first frequency range or the second frequency range as a function of a desired in vivo penetration depth.

13. A method of operating an ultrasound device comprising a semiconductor die having an array of capacitive micromachined ultrasonic transducers (CMUTs), the method comprising:
    using a controller integrated on the semiconductor die with the array of CMUTs to:
    in response to receiving an indication to operate in a first mode of operation having an associated first frequency range of operation,
        select, from among a plurality of selectable active apertures occupying different physical areas of the semiconductor die, using information specifying, for the first mode of operation, a first azimuth aperture value or a first elevation aperture value, a first active aperture associated with the first mode of operation of the ultrasound device and representing a first set of CMUTs of the array occupying a first physical area of the different physical areas of the semiconductor die; and
        generate and detect ultrasound signals having frequencies within the first frequency range with the CMUTs of the first active aperture; and
    in response to receiving an indication to operate in a second mode of operation having an associated second frequency range of operation different from the first frequency range of operation,
        select, from among the plurality of selectable active apertures, using information specifying, for the second mode of operation, a second azimuth aperture value different from the first azimuth aperture value or a second elevation aperture value different from the first elevation aperture value, a second active aperture associated with the second mode of operation of the ultrasound device and representing a second set of CMUTs of the array occupying a second physical area of the different physical areas of the semiconductor die; and
        generate and detect ultrasound signals having frequencies within the second frequency range with the CMUTs of the second active aperture;
        wherein: (a) both the first and second modes of operation comprise collapse modes of operation; or (b) both the first and second modes of operation comprise non-collapsed modes of operation.

14. The method of claim 13, wherein the first set of CMUTs and the second set of CMUTs overlap.

15. The method of claim 13, wherein the first set of CMUTs and the second set of CMUTs do not overlap.

16. The method of claim 13, wherein the first frequency range and the second frequency range overlap.

17. The method of claim 13, wherein the first frequency range and the second frequency range do not overlap.

18. The method of claim 13, wherein the first frequency range is in a range of about 1-5 MHz, with a center frequency of about 3 MHz.

19. The method of claim 13, wherein the first frequency range is powered to penetrate an approximate depth of about 10-25 cm within a subject.

20. The method of claim 13, wherein the second frequency range is in a range of about 5-12 MHz, with a center frequency of about 8 MHz.

21. The method of claim 13, wherein the second frequency range is powered to penetrate an approximate depth of about 1-10 cm within a subject.

22. The method of claim 13, further comprising operating the array in a third frequency range using a third selectable active aperture.

23. The method of claim 22, wherein the first frequency range is about 1-3 MHz, the second frequency range is about 3-7 MHz and the third frequency range is about 7-12 MHz.

24. The method of claim 22, wherein the first frequency range is about 1-5 MHz, the second frequency range is about 3-7 MHz and the third frequency range is about 5-10 MHz.

25. The method of claim 13, wherein the first frequency range and the second operating frequency range are used in connection with different elevational focal regions.

26. The method of claim 13, wherein selecting the first active aperture is done as a function of a desired in vivo penetration depth.

\* \* \* \* \*

UNITED STATES PATENT AND TRADEMARK OFFICE
CERTIFICATE OF CORRECTION

PATENT NO. : 10,856,840 B2
APPLICATION NO. : 15/415434
DATED : December 8, 2020
INVENTOR(S) : Jonathan M. Rothberg et al.

Page 1 of 1

It is certified that error appears in the above-identified patent and that said Letters Patent is hereby corrected as shown below:

In the Claims

In Claim 25 at Column 29, Line 17 please delete "operating".

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*